(12) United States Patent
Venkataraman et al.

(10) Patent No.: US 7,943,781 B2
(45) Date of Patent: May 17, 2011

(54) PROCESS FOR PREPARING TELMISARTAN

(75) Inventors: Sundaram Venkataraman, Hyderabad (IN); Vijayavitthal Thippannachar Mathad, Hyderabad (IN); Srirami Reddy Kikkuru, Guntur dist. (IN); Srinivasan Neti, Bhimavaram (IN); Raveendra Reddy Chinta, Chittoor (IN); Muthulingam Arunagiri, Hyderabad (IN); Lalitha Kumari Routhu, Hyderabad (IN)

(73) Assignees: Dr. Reddy's Laboratories Limited, Hyderabad, Andhra Pradesh (IN); Dr. Reddy's Laboratories, Inc., Bridgewater, NJ (US)

( * ) Notice: Subject to any disclaimer, the term of this patent is extended or adjusted under 35 U.S.C. 154(b) by 550 days.

(21) Appl. No.: 11/577,452

(22) PCT Filed: Oct. 18, 2005

(86) PCT No.: PCT/US2005/037185
§ 371 (c)(1),
(2), (4) Date: Apr. 18, 2007

(87) PCT Pub. No.: WO2006/044754
PCT Pub. Date: Apr. 27, 2006

(65) Prior Publication Data
US 2007/0287840 A1    Dec. 13, 2007

(51) Int. Cl.
*C07D 235/08*    (2006.01)
(52) U.S. Cl. .................................................. 548/310.1
(58) Field of Classification Search ............... 548/305.4, 548/310.1
See application file for complete search history.

(56) References Cited

U.S. PATENT DOCUMENTS

| | | |
|---|---|---|
| 5,591,762 A | 1/1997 | Hauel |
| 6,358,986 B1 | 3/2002 | Schneider |
| 6,410,742 B1 | 6/2002 | Schneider |
| 6,737,432 B2 | 5/2004 | Donsbach |
| 6,770,762 B2 | 8/2004 | Belzer |
| 2002/0094997 A1 | 7/2002 | Schneider |
| 2003/0130331 A1 | 7/2003 | Donsbach |
| 2003/0139608 A1 | 7/2003 | Belzer |
| 2004/0162327 A1 | 8/2004 | Donsbach |
| 2004/0225129 A1 | 11/2004 | Belzer |
| 2004/0236113 A1 | 11/2004 | Hauel |

FOREIGN PATENT DOCUMENTS

| | | |
|---|---|---|
| CA | 2 524 091 A1 | 11/2004 |
| WO | WO0043370 A1 | 7/2000 |
| WO | WO03037876 A1 | 5/2003 |
| WO | WO03059890 A1 | 7/2003 |
| WO | WO2004087676 A1 | 10/2004 |

*Primary Examiner* — Shawquia Young
(74) *Attorney, Agent, or Firm* — Robert A. Franks; Balaram Gupta; Thomas C. McKenzie

(57) ABSTRACT

A process comprising cyclizing 3-amino-4-butyramido-5-methylbenzoic acid to form 2-n-propyl-4-methyl-benzimidazole-6-carboxylic acid.

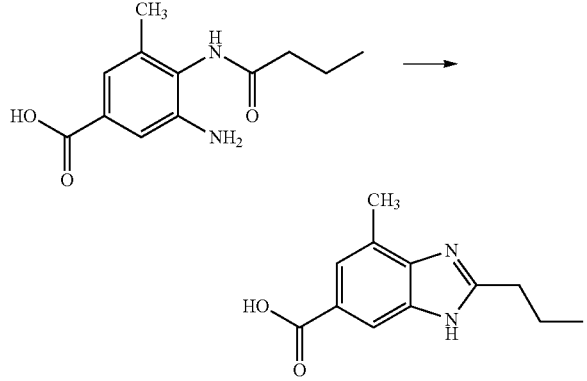

8 Claims, 7 Drawing Sheets

PROCESS FOR PREPARING TELMISARTAN

The present invention relates to processes for preparing telmisartan, telmisartan salts, and intermediates thereof.

Telmisartan is chemically known as 4'-[[(2-n-propyl-4-methyl-6-(1-methylbenzimidazol-2-yl)-benzimidazol-1-yl]-methyl]-biphenyl-2-carboxylic acid, and has the following structural Formula I.

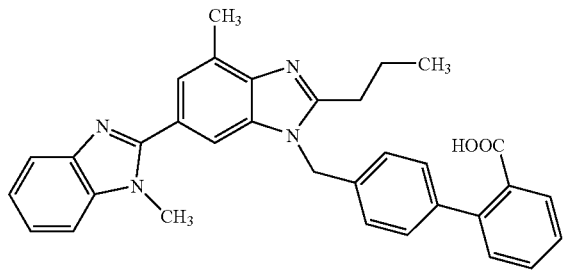

Formula I

Telmisartan is an angiotensin-II receptor antagonist, useful in the treatment of hypertensive diseases, heart diseases, heart strokes and bladder diseases and is commercially available in tablets sold using the brand name MICARDIS™.

U.S. Pat. No. 5,591,762 discloses telmisartan and its pharmaceutically acceptable salts, along with pharmaceutical compositions. This patent also discloses a process for the preparation of telmisartan by hydrolysing the tertiary-butyl ester precursor of telmisartan with trifluoroacetic acid in dimethylformamide.

The aforementioned process has some disadvantages like lengthy maintenance of the reaction, low purity of the resultant compound and usage of hazardous chemicals like trifluoroacetic acid.

The solvents used in the preparation of a drug substance sometimes cannot completely be removed by practical manufacturing techniques, which are employed in the production. Therefore, in the preparation of a drug substance wherein plural steps are serially carried out until the final step, each solvent used in each step can possibly remain present as a residue in the drug substance. Further, solvent residues in a drug substance usually are not useful for the therapeutic benefits of the drug substance, and actually may cause a problem of safety to a patient, depending on the kinds of residual solvents and concentrations thereof. For improving and increasing the safety of drugs, the International Conference on Harmonization of Technical Requirements for Registration of Pharmaceuticals for Human Use published its recommendations as "IMPURITIES: GUIDELINE FOR RESIDUAL SOLVENTS Q3C," ICH Harmonized Tripartite Guideline, on 17 Jul. 1997. These recommendations have been adopted by regulatory authorities in the European Union, Japan, and the USA.

Since a solvent can play an important role in increasing the yield rate or in determination of physical properties of drug substance such as the crystal form, purity, solubility, etc., even if such a solvent is known to be toxic, there may be many cases where the use thereof in the preparation of drug substance cannot be avoided in terms of risk-benefits. In such cases, this guideline requires that a concentration of a residual solvent in drug substance should be not more than a specified value, which is toxicologically acceptable.

Consequently, there is a long-felt need for a process for proficiently preparing intermediates of telmisartan free of impurities and telmisartan that is substantially free of residual solvent, ash, and impurities.

SUMMARY OF THE INVENTION

In one aspect, the invention provides a process for the preparation of telmisartan.

In another aspect, the invention relates to a process for proficiently preparing telmisartan substantially free of residual solvent.

In a further aspect, the invention relates to a process for proficiently preparing telmisartan substantially free of ash content.

In a still further aspect, the invention provides telmisartan and intermediates of telmisartan substantially free of impurities.

In an additional aspect, the invention provides polymorphic forms of methyl-4'-[[(2-n-propyl-4-methyl-6-(1-methylbenzimidazol-2-yl)-benzimidazol-1-yl]-methyl]-biphenyl-2-carboxylate and it's hydrochloride salt, and process for the preparation thereof.

In an aspect, the invention provides a process for preparing telmisartan, comprising:

a) reduction of methyl 4-butyramido-3-methyl-5-nitrobenzoate to form methyl 3-amino-4-butyramido-5-methylbenzoate, which on subsequent hydrolysis followed by ring closure forms 2-n-propyl-4-methyl-benzimidazole-6-carboxylic acid;

b) condensation of 2-n-propyl-4-methyl-benzimidazole-6-carboxylic acid with N-methyl-o-phenylenediamine hydrochloride to form 2-n-propyl-4-methyl-6-(1-methyl benzamidazole-2-yl)benzamidazole;

c) condensation of 2-n-propyl-4-methyl-6-(1-methyl benzamidazole-2-yl)benzamidazole with methyl 4'-(bromomethyl)biphenyl-2-carboxylate in the presence of a base to form methyl-4'-[(2 n-propyl-4-methyl-6-(1-methylbenzimidazol-2-yl)-benzimidazol-1-yl)-methyl]-biphenyl-2-carboxylate;

d) hydrolysis of methyl-4'-[[(2 n-propyl-4-methyl-6-(1-methylbenzimidazol-2-yl)-benzimidazol-1-yl]-methyl]-biphenyl-2-carboxylate, or its acid addition salt, with a base to form telmisartan; and e) purifying to afford pure telmisartan.

In another aspect of the present invention, there is provided an alternative process for the preparation of 2-n-propyl-4-methyl-benzimidazole-6-carboxylic acid of Formula III.

In yet another aspect, the process of the present invention provides alternative methods for the preparation of 2-n-propyl-4-methyl-6-(1-methyl benzamidazole-2-yl)benzamidazole of Formula IV.

Another aspect of the invention provides a crystalline potassium salt of telmisartan.

Another additional aspect of the invention provides a crystalline telmisartan hydrogen sulphate.

In further aspect, the present invention provides compounds of formulae:

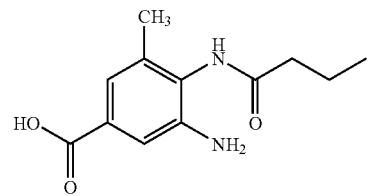
Formula IIb

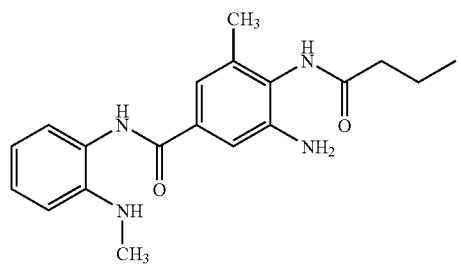
Formula IIIb

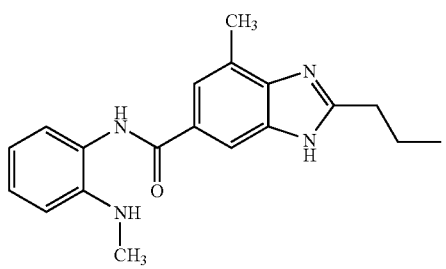
Formula IVa

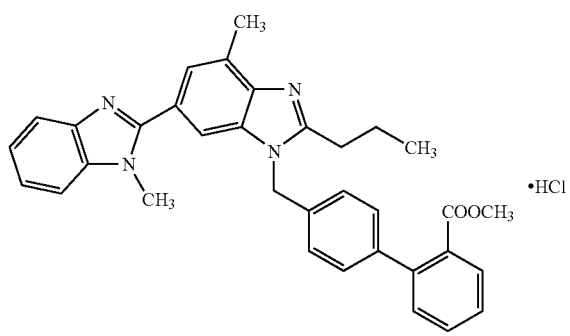
Formula VI

In a still further aspect, the invention provides processes for the preparation of compounds IIb, IIIb, IVa and VI.

The invention also provides telmisartan containing low concentrations of any one or more of:
i) Methyl-(2-n-propyl-4-methyl-1-hydroxy benzimidazole)-6-carboxylate;
ii) (2-n-propyl-4-methyl-1-hydroxy benzimidazole)-6-carboxylic acid;
iii) N-methyl-2-nitroso aniline;
iv) o-Phenylene diamine;
v) N6-[2-(methylamino)phenyl]-3-amino-4-methyl-2-propyl benzo diimidazole-6-carboxamide;
vi) N1-[2-(methylamino)phenyl]-3-amino-4-butyramino-5-methyl benzamide;
vii) 2-n-propyl-4-methyl-6-(1-benzimidazole-2-yl)benzimidazole;
viii) 2-n-propyl-4-methyl-6-(1-methyl benzimidazole-2-yl)-1-hydroxy benzimidazole;
ix) Methyl 4¹,4¹-dibromo methyl biphenyl-2-carboxylate;
x) Methyl 4'-[2-n-propyl-4-methyl-6-carboxylic acid-benzimidazol-1-yl]-methyl-biphenyl-2-carboxylate;
xi) 4'-[2-n-propyl-4-methyl-6-carboxylic acid-benzimidazol-1-yl]-methyl-biphenyl-2-carboxylic acid;
xii) Methyl 4'-[2-n-propyl-4-methyl-6 {methyl-4"-(1-methyl-biphenyl-2'carboxylate)benzimidazol-2-yl}-benzimidazol-1-yl]-methyl-biphenyl-2-carboxylate; and
xiii) 4'-[2-n-propyl-4-methyl-6 {4"-(1-methyl-biphenyl-2-carboxylic acid)benzimidazol-2-yl}-benzimidazol-1-yl]-methyl-biphenyl-2-carboxylic acid.

DETAILED DESCRIPTION OF THE INVENTION

Figure 1:
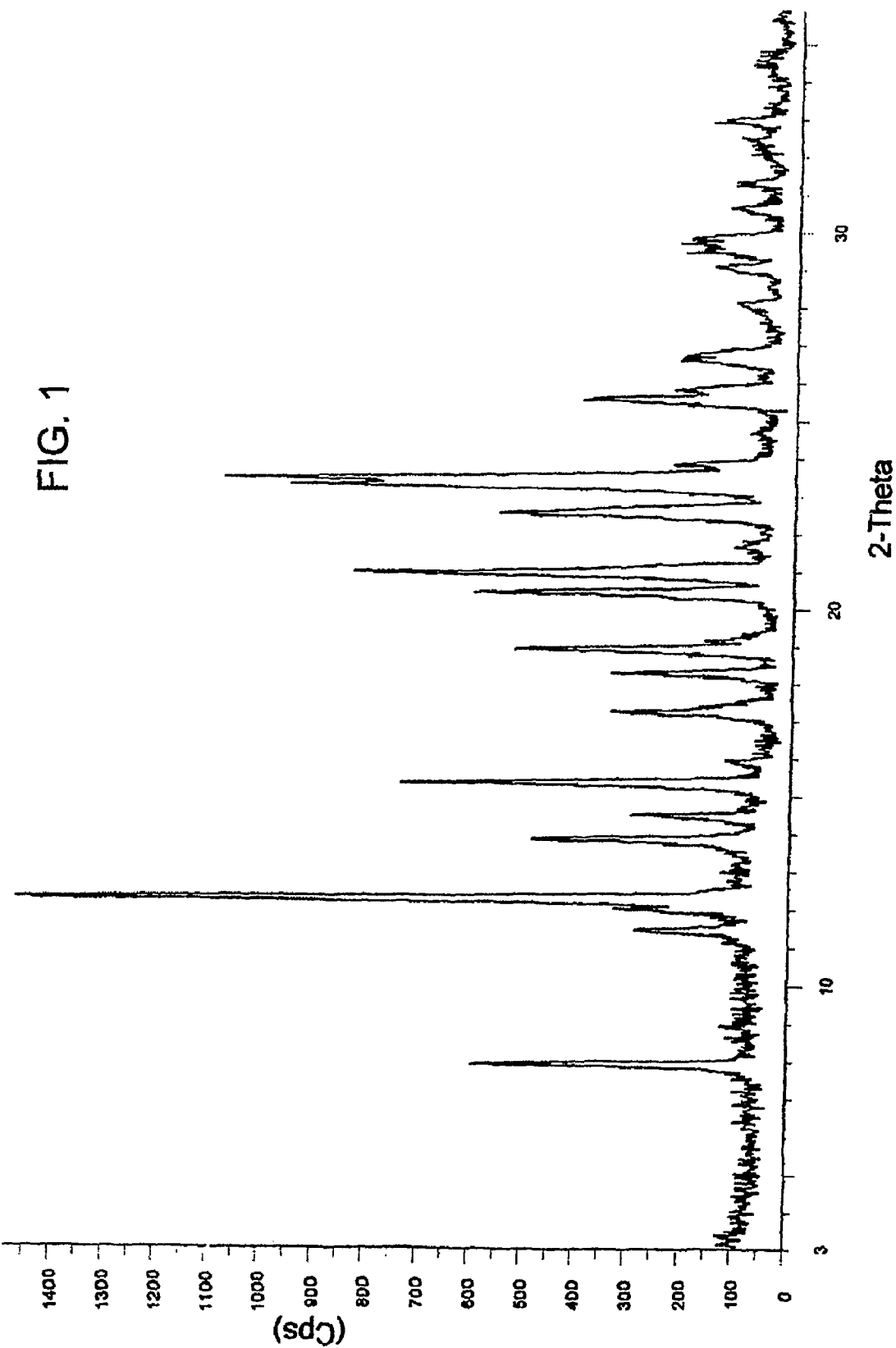
FIG. 1 is an X-ray powder diffraction ("XRPD") pattern for crystalline Form A of methyl-4'-[[(2 n-propyl-4-methyl-6-(1-methylbenzimidazol-2-yl)-benzimidazol-1-yl]-methyl]-biphenyl-2-carboxylate.

In one aspect, the invention provides a process for the preparation of telmisartan.

In another aspect, the invention relates to a process for proficiently preparing telmisartan free of residual solvent.

In a further aspect, the invention relates to a process for proficiently preparing telmisartan substantially free of ash.

In a still further aspect, the invention provides telmisartan and intermediates of telmisartan substantially free of impurities.

The present invention, in one aspect, relates to a process for the preparation of telmisartan of Formula I comprising the steps of:

a) reduction of the methyl 4-butyramido-3-methyl-5-nitrobenzoate compound of Formula II,

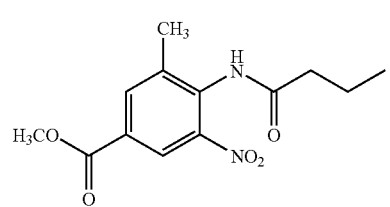
Formula II by hydrogenation, such as using palladium on charcoal in a solvent such as methanol, to give methyl 3-amino-4-butyramido-5-methylbenzoate of Formula IIa,

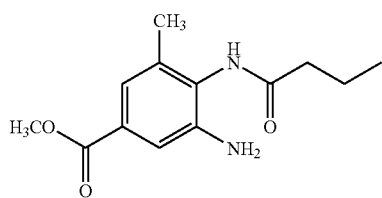

Formula IIa which on subsequent hydrolysis followed by ring closure with a suitable base in a suitable solvent gives 2-n-propyl-4-methyl-benzimidazole-6-carboxylic acid of Formula III;

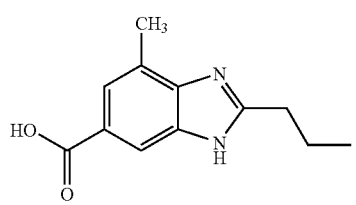

Formula III b) condensation of 2-n-propyl-4-methyl-benzimidazole-6-carboxylic acid of Formula III with N-methyl-o-phenylenediamine hydrochloride of Formula IIIa

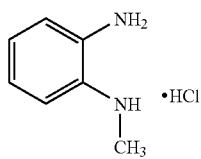

Formula IIIa in the presence of a suitable reagent, to give 2-n-propyl-4-methyl-6-(1-methyl benzamidazole-2-yl)benzamidazole of Formula IV;

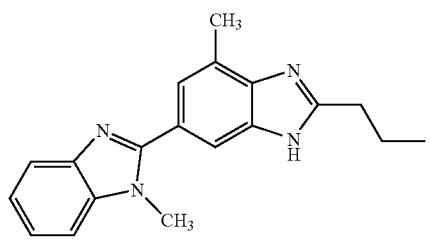

Formula IV c) condensation of 2-n-propyl-4-methyl-6-(1-methyl benzamidazole-2-yl)benzamidazole of Formula IV with methyl 4'-(bromomethyl)biphenyl-2-carboxylate of Formula V,

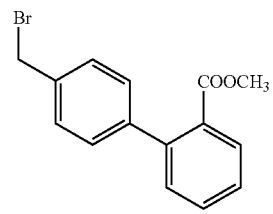

Formula V in the presence of a suitable base in a suitable solvent to give methyl-4'-[[(2 n-propyl-4-methyl-6-(1-methylbenzimidazol-2-yl)-benzimidazol-1-yl]-methyl]-biphenyl-2-carboxylate of Formula VI;

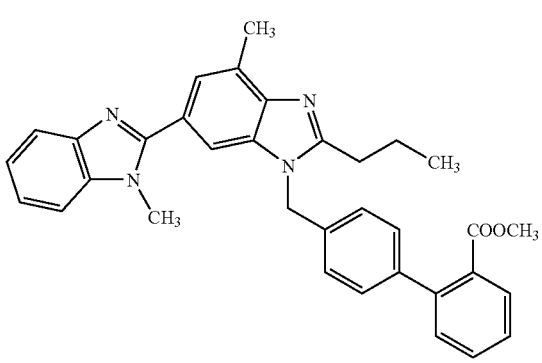

Formula VI d) hydrolysis of methyl-4'-[[(2 n-propyl-4-methyl-6-(1-methylbenzimidazol-2-yl)-benzimidazol-1-yl]-methyl]-biphenyl-2-carboxylate of Formula VI or its acid addition salt in the presence of a suitable base in a suitable solvent to form telmisartan; and e) purifying as necessary to afford pure telmisartan.

Step a) involves hydrogenation of the methyl 4-butyramido-3-methyl-5-nitro benzoate compound of Formula II with palladium on charcoal (containing about 50% water) in methanol to give methyl 3-amino-4-butyramido-5-methyl-benzoate of Formula IIa, which on subsequent hydrolysis followed by ring closure with a suitable base in a suitable solvent gives 2-n-propyl-4-methyl-benzimidazole-6-carboxylic acid of Formula III.

Suitable inorganic bases that can be used in the reaction include but are not limited to: hydroxides of alkali metals such as lithium hydroxide, sodium hydroxide, potassium hydroxide, and the like; carbonates of alkali metals such as sodium carbonate, potassium carbonate, and the like; and bicarbonates of alkali metals such as sodium bicarbonate, potassium bicarbonate, and the like.

Suitable solvents that can be used in the hydrolysis include but are not limited to: alcoholic solvents such as methanol, ethanol, isopropanol, and the like; water; and their mixtures.

The temperature for conducting the hydrolysis can range from 50-110° C., or 60-100° C., or at the reflux temperature of the solvent used.

The intermediate compound of Formula IIa in step a) may or may not be isolated. The same can be converted in situ to the compound of Formula III.

It has been found that the compound of Formula III is substantially free of methyl-(2n-propyl-4-methyl-1-hydroxy benzimidazole)-6-carboxylate and contains low concentrations of 2-n-propyl-4-methyl-1-hydroxy benzimidazole)-6- carboxylic acid, i.e., such as less than or equal to about 0.15 area-%, or less than about 0.12 area-%, as determined by high performance liquid chromatography ("HPLC").

Step b) involves condensation of 2-n-propyl-4-methyl-benzimidazole-6-carboxylic acid of Formula III with N-methyl-o-phenylenediamine hydrochloride of Formula IIIa, in the presence of a suitable condensation reagent, to give 2-n-propyl-4-methyl-6-(1-methyl benzamidazole-2-yl)benzamidazole of Formula IV.

The condensation reaction can also be carried out by using known methods, such as described by U. J. Ries et al., in *Journal of Medicinal Chemistry*, Vol. 36, pages 4040-4051 (1993), and U.S. Pat. No. 6,770,762.

It has been found that the compound of Formula IV is substantially free of N6-[2-(methylamino)phenyl]-3-amino-4-methyl-2-propyl benzodiimidazole-6-carboxamide, N1-[2-(methylamino)phenyl]-3-amino-4-(butyramino)-5-methyl benzamide, 2-n-propyl-4-methyl-6-(1-methyl benzimidazole-2-yl)-1-hydroxy benzimidazole, and contains low concentrations of 2-n-propyl-4-methyl-6-(1-benzimidazole-2-yl)benzimidazole, such as less than or equal to about 0.5 area-%, or less than about 0.28 area-%, by HPLC.

Step c) involves condensation of 2-n-propyl-4-methyl-6-(1-methyl benzamidazole-2-yl)benzamidazole of Formula IV with methyl 4'-(bromo methyl)biphenyl-2-carboxylate of Formula V in the presence of a suitable base in a suitable solvent to give methyl-4'-[[(2-n-propyl-4-methyl-6-(1-methyl benzimidazol-2-yl)-benzimidazol-1-yl]-methyl]-biphenyl-2-carboxylate of Formula VI.

Bases that are useful for the reaction include: inorganic bases like hydroxides of alkali metals such as lithium hydroxide, sodium hydroxide, potassium hydroxide and the like, carbonates of alkali metals such as sodium carbonate, potassium carbonate, and the like, and bicarbonates of alkali metals such as sodium bicarbonate, potassium bicarbonate, and the like; and organic bases such as triethylamine, tributylamine, tripropylamine, and the like.

Solvents that can be used in the reaction include, without limitation: ketone solvents such as acetone, diethyl ketone, methyl isobutyl ketone (MIBK), and the like; nitrile solvents such as acetonitrile, propionitrile and the like; alcoholic solvents such as methanol, ethanol, propanol, butanol, and the like; tetrahydrofuran; and water; and mixtures thereof;

Suitable temperatures for conducting the reaction can range from 0-100° C., or 10-50° C., or 20-30° C.

The compound having Formula VI can be converted to its acid addition salt, by reacting with an acidic reagent, such as with alcoholic or aqueous hydrochloric acid to form the hydrochloride salt.

It has been found that the compound of Formula VI contains low concentrations of Methyl 4'-[2-n-propyl-4-methyl-6-carboxylic acid-benzimidazol-1-yl]-methyl-biphenyl-2-carboxylate, 4'-[2-n-propyl-4-methyl-6-carboxylic acid-benzimidazol-1-yl]-methyl-biphenyl-2-carboxylic acid, and Methyl 4'-[2-n-propyl-4-methyl-6{methyl-4"-(1-methyl-biphenyl-2'carboxylate)benzimidazol-2-yl}-benzimidazol-1-yl]-methyl-biphenyl-2-carboxylate, such as less than or equal to about 0.1 area-%, or less than about 0.05 area-%, by HPLC.

Step d) involves hydrolysis of methyl-4'-[[(2-n-propyl-4-methyl-6-(1-methylbenzimidazol-2-yl)-benzimidazol-1-yl]-methyl]-biphenyl-2-carboxylate of Formula VI, or its acid addition salt, in the presence of a suitable base in a suitable solvent to give telmisartan.

Bases that are useful for the reaction include: hydroxides of alkali metals such as lithium hydroxide, sodium hydroxide, potassium hydroxide, and the like; carbonates of alkali metals such as sodium carbonate, potassium carbonate, and the like; and bicarbonates of alkali metals such as sodium bicarbonate, potassium bicarbonate, and the like.

Suitable solvents for the reaction include nitrile solvents such as acetonitrile, propionitrile, and the like.

Temperatures for conducting the reaction can range from 0-150° C., or 50-100° C., or at the reflux temperature of the solvent used.

In one embodiment, the potassium salt of telmisartan may or may not be isolated. The potassium salt of telmisartan can be isolated by filtration, centrifugation, decantation, and the like.

The potassium salt of telmisartan can be further converted to telmisartan by heating the potassium salt of telmisartan in suitable solvents, followed by adjusting the pH using a suitable acid.

Solvents that can be used include, but are not limited to, organic solvents such as nitrile solvents like acetonitrile, propionitrile, and the like; water; or mixtures thereof.

Suitable acids can be aqueous. An example of a suitable acid is acetic acid.

The pH can depend on the acid. A suitable pH range is typically 5-5.5.

It has been observed that telmisartan obtained from the step d) frequently contains ash, in an amount about 3% w/w.

In one embodiment, telmisartan hydrogen sulphate is obtained wherein the acid is sulfuric acid and pH is less than 5.

Step e) involves purification of telmisartan comprising the steps of:
  i) dissolving crude telmisartan in a solvent, and crystallizing;
  ii) crystallization in a mixture of solvents; and
  iii) recrystallization in an organic solvent.

Step i) of e) involves dissolving crude telmisartan in a suitable solvent. A suitable solvent can be water. A suitable temperature range is from 50 to 80° C. The solution containing crude telmisartan can be cooled to 20 to 55° C., or 40-50° C. for crystallization. The solid is then separated, such as by filtration followed by washing with a suitable solvent such as water. The obtained material is dried by using the technique known in art at 50 to 90° C. over a period of 4 to 6 hours to afford telmisartan.

It has been observed that telmisartan obtained from the step i) contains ash in an amount typically less than about 1% w/w.

Step ii) of e) involves crystallization of telmisartan from step i) in a mixture of solvents.

The solvents that can be used for this crystallization include halogenated hydrocarbons, alcohols, or mixtures thereof. Examples of halogenated solvents are dichloromethane, chloroform, ethylene dichloride, and the like. Useful alcoholic solvents include methanol, ethanol, isopropanol, butanol, and the like.

It has been found that telmisartan obtained from step ii) is substantially free from extraneous matter, i.e. is substantially particle free, ash free, etc., but the residual solvent content can be high, such as more than about 6000 ppm of dichloromethane. It has been observed that telmisartan obtained from step ii) typically contains ash less than about 0.1% w/w.

Step iii) of e) involves recrystallization of telmisartan in an organic solvent. Useful organic solvents include, but are not limited to, alcohol solvents such as methanol, ethanol, isopropanol, butanol, and the like.

It has been surprisingly found that telmisartan obtained by the above process is substantially free from residual solvents such as dichloromethane, e.g., containing less than about 500 ppm, or less than about 150 ppm, or less than about 50 ppm of solvent, and contains less than about 0.1% w/w of ash.

It has been found that the telmesartan subjected to step e) is substantially free of 4'-[2-n-propyl-4-methyl-6{4''-(1-methyl-biphenyl-2-carboxylic acid) benzimidazol-2-yl}-benzimidazol-1-yl]-methyl-biphenyl-2-carboxylic acid.

The whole process can be represented by the following Scheme A:

b) cyclisation of 3-amino-4-butyramido-5-methylbenzoic acid of Formula IIb in the presence of a dehydrating agent to give 2-n-propyl-4-methyl-benzimidazole-6-carboxylic acid of Formula III.

A suitable inorganic base for use in step a) includes but is not limited to: hydroxides of alkali metals such as lithium

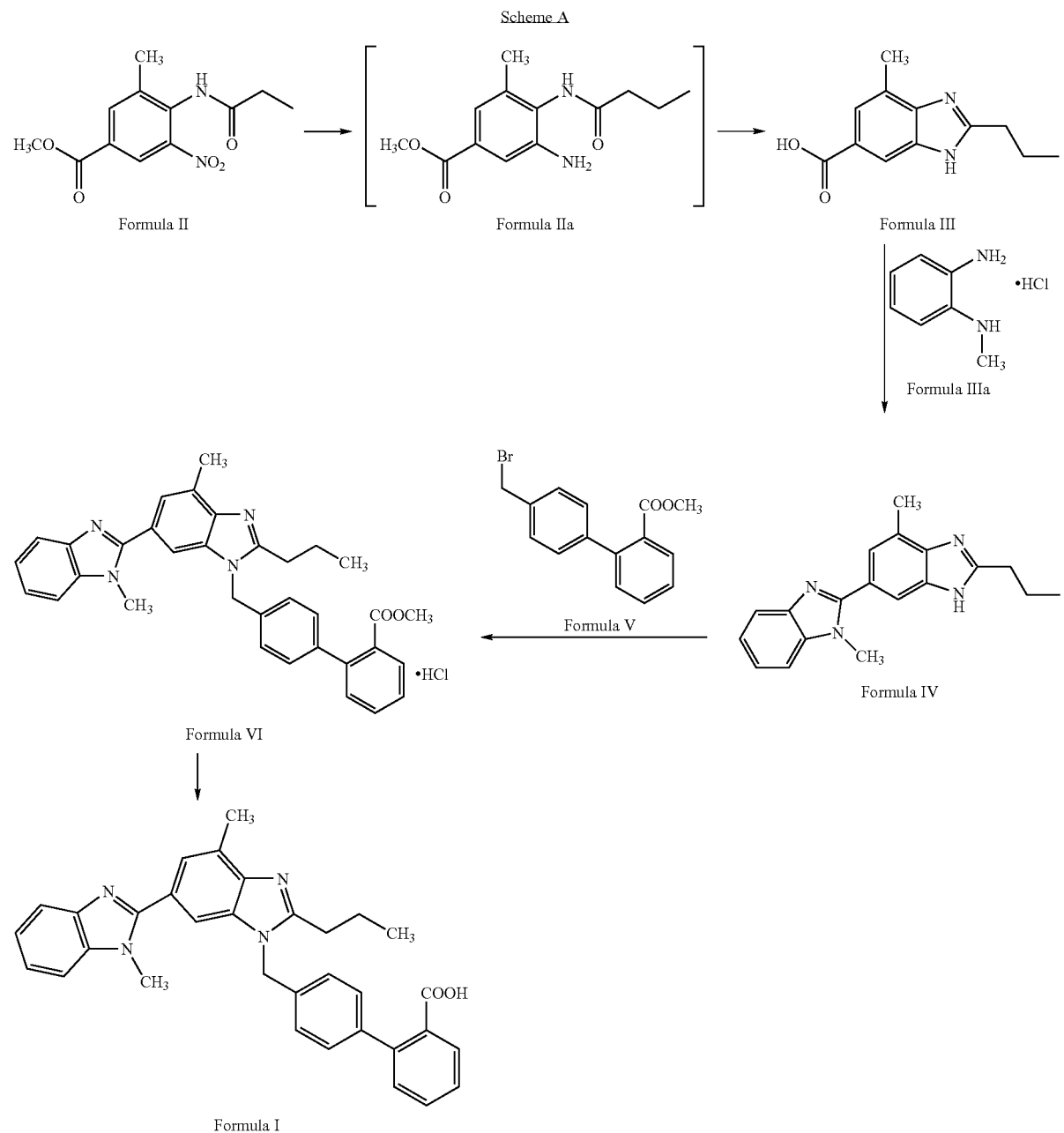

Scheme A

In another aspect of the present invention, there is provided an alternative process for the preparation of 2-n-propyl-4-methyl-benzimidazole-6-carboxylic acid of Formula III, comprising the steps of:
  a) hydrolysis of methyl 3-amino-4-butyramido-5-methylbenzoate of Formula IIa by reaction with an inorganic base in the presence of alcohol and water, to give 3-amino-4-butyramido-5-methylbenzoic acid of Formula IIb;

hydroxide, sodium hydroxide, potassium hydroxide and the like; carbonates of alkali metals such as sodium carbonate, potassium carbonate and the like; and bicarbonates of alkali metals such as sodium bicarbonate, potassium bicarbonate and the like.

A suitable alcohol for use in the hydrolysis includes methanol, ethanol, isopropanol and the like. The temperature for conducting the reaction can range from 0-100° C., or 25-75° C., or 60-65° C.

A suitable dehydrating agent for use in step b) includes acetic acid, polyphosphoric acid (PPA), methane sulfonic acid and the like.

The whole process is represented by the following Scheme B:

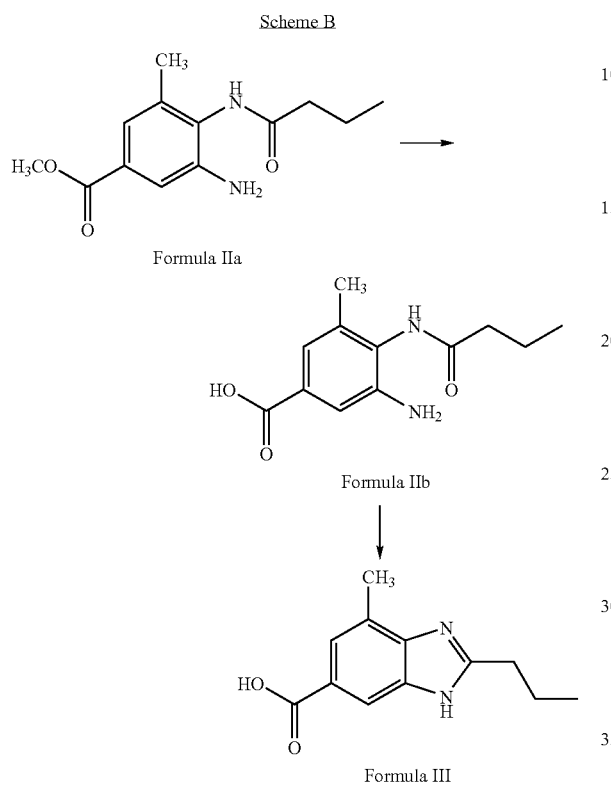

In yet another aspect, the process of the present invention provides an alternative method for the preparation of 2-n-propyl-4-methyl-6-(1-methyl benzamidazole-2-yl)benzamidazole of Formula IV, without preparation of the compound of Formula III, comprising the steps of:
  a) condensation of 3-amino-4-butyramido-5-methylbenzoic acid of Formula IIb with N-methyl-o-phenylenediamine of Formula IIIa, in the presence of a suitable condensation reagent in a suitable solvent to give 3-amino-4-(butyramido)-5-methyl-N-(2-(methylamino)phenyl)benzamide of Formula IIIb;
  b) cyclisation of 3-amino-4-butyramido-5-methyl-N-(2-(methylamino)phenyl)benzamide of Formula IIIb in the presence of a dehydrating agent to give the compound of formula IV.

A condensation reagent useful for step a) is dicyclohexyl carbodiimide (DCC), optionally in combination with 1-hydroxy benzotriazole (HOBT), and optionally in the presence of a catalytic amount of dimethylamino pyridine (DMAP).

A suitable solvent for this step a) includes any solvent or mixture of solvents, in which required components are soluble. Examples include dimethylformamide (DMF); dimethylsulfoxide (DMSO); dimethylacetamide (DMAC); and the like; chlorohydrocarbon solvents having $C_1$-$C_4$-carbon atoms such as dichloromethane, ethylene dichloride, chloroform and the like; or mixtures thereof.

Suitable dehydrating agents that are useful in step b) include acetic acid, polyphosphoric acid (PPA), methane sulfonic acid and the like.

The whole process is represented by the following Scheme C

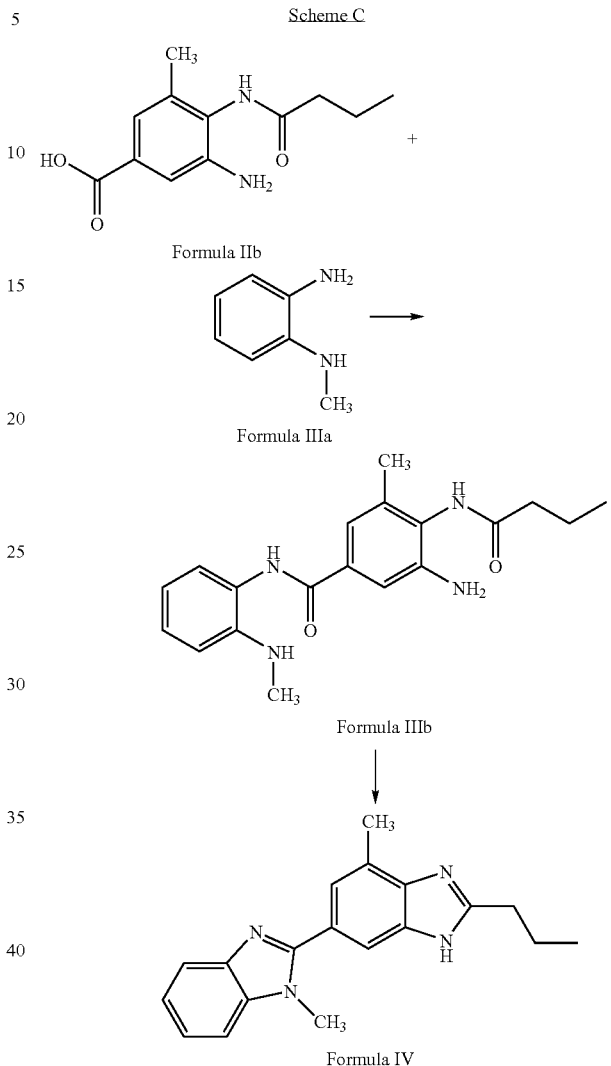

In one more aspect, the present invention provides an alternative process for the preparation of the compound of Formula IV, comprising the steps of;
  a) condensing 2-n-propyl-4-methyl-benzimidazole-6-carboxylic acid of Formula III with N-methyl-o-phenylenediamine of Formula IIIa, in the presence of a suitable condensation reagent, to give 7-methyl-N-(2-(methylamino)phenyl)-2-propyl-3H-benzodiimidazole-5-carboxamide of Formula IVa; and
  b) cyclisation of the compound of Formula IVa in the presence of a dehydrating agent giving the compound of Formula IV.

A condensation reagent useful for step a) is dicyclohexylcarbodiimide (DCC), optionally in combination with 1-hydroxy benzotriazole (HOBT), optionally in the presence of a catalytic amount of dimethylaminopyridine (DMAP).

Suitable solvents for this reaction include any solvent or mixture of solvents, in which required components are soluble. Examples include, without limitation thereto, dimethylformamide (DMF), dimethylsulfoxide (DMSO), dimethylacetamide (DMAC), and the like; $C_1$-$C_4$ chlorohydrocarbon solvents such as dichloromethane, ethylenedichloride, chloroform, and the like; or mixtures thereof.

A suitable dehydrating agent that is used in step b) includes acetic acid, polyphosphoric acid (PPA), methane sulfonic acid, and the like.

The whole process can be represented by the following Scheme D:

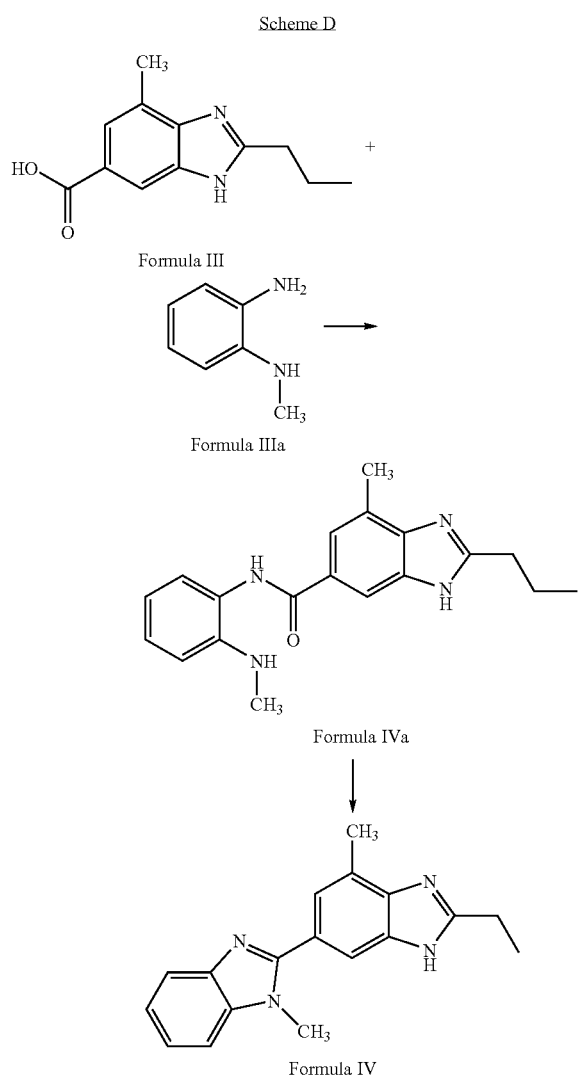

A further aspect of the present invention relates to acid addition salts of methyl-4'-[[(2-n-propyl-4-methyl-6-(1-methylbenzimidazol-2-yl)-benzimidazol-1-yl]-methyl]-biphenyl-2-carboxylate of Formula VI, and a process for preparation thereof.

The acid addition salts include, without limitation, hydrochloride, hydrobromide, hydrogen sulfate, tosylate, fumarate, maleate, tartrate, and methane sulfonate salts, and the like.

For purposes of the present invention, the hydrochloride salt is well suited for commercial production of telmisartan with high purity, without further purification. The hydrochloride salt of the compound of Formula VI exhibits a high degree of crystallinity with good flow properties and stability, making it easy to handle on a commercial scale.

The hydrochloride salt of the compound of Formula VI is prepared by reaction of the free base obtained by step c) of Scheme A, with hydrochloric acid in a suitable solvent. A suitable reagent for this purpose includes methanolic hydrochloric acid, isopropanolic hydrochloric acid, ethyl acetate hydrochloride, aqueous hydrochloric acid, and the like.

In yet another aspect, the present invention relates to polymorphic forms of methyl-4'-[[(2-n-propyl-4-methyl-6-(1-methylbenzimidazol-2-yl)-benzimidazol-1-yl]-methyl]-biphenyl-2-carboxylate of Formula VI and its hydrochloride salt, and processes for the preparation thereof.

The compound methyl-4'-[[(2-n-propyl-4-methyl-6-(1-methylbenzimidazol-2-yl)-benzimidazol-1-yl]-methyl]-biphenyl-2-carboxylate of Formula VI, as well as its hydrochloride salt, were found to exist in both crystalline and amorphous forms.

The crystalline form (herein after referred to as "Form A") of methyl-4'-[[(2-n-propyl-4-methyl-6-(1-methyl benzimidazol-2-yl)-benzimidazol-1-yl]-methyl]-biphenyl-2-carboxylate of Formula VI, is characterized by the XRPD pattern of FIG. 1, wherein the most characteristic peaks are at about 7.8, 11.3, 12.2, 13.8, 14.4, 15.3, 17.2, 18.2, 18.9, 20.4, 20.9, 22.5, 23.3, 23.4, 23.8, 25.5, 25.8, 26.6, 29.0, 29.8 and 32.95±0.2 degrees two theta.

A process for preparing crystalline Form A of the compound of Formula VI comprises:
 a) heating a mixture of about 4 parts by weight methyl-4'-[[(2-n-propyl-4-methyl-6-(1-methyl benzimidazol-2-yl)-benzimidazol-1-yl]-methyl]-biphenyl-2-carboxylate and about 40 parts by weight acetonitrile to reflux;
 b) stirring at reflux, such as for about 30-60 minutes, to form a solution;
 c) distilling off a portion of the solvent, such as about 50%, from the solution of step b) under reduced pressure;
 d) cooling the solution of step c) to 20-40° C. and stirring as crystals form, such as for about 30-60 minutes;
 e) filtering the separated solid from step d) and washing with acetonitrile; and
 f) drying the obtained solid from step e) at about 45-60° C., such as for about 3-5 hours, to get the crystalline Form A of methyl-4'-[[(2-n-propyl-4-methyl-6-(1-methylbenzimidazol-2-yl)-benzimidazol-1-yl]-methyl]-biphenyl-2-carboxylate.

Figure 3:
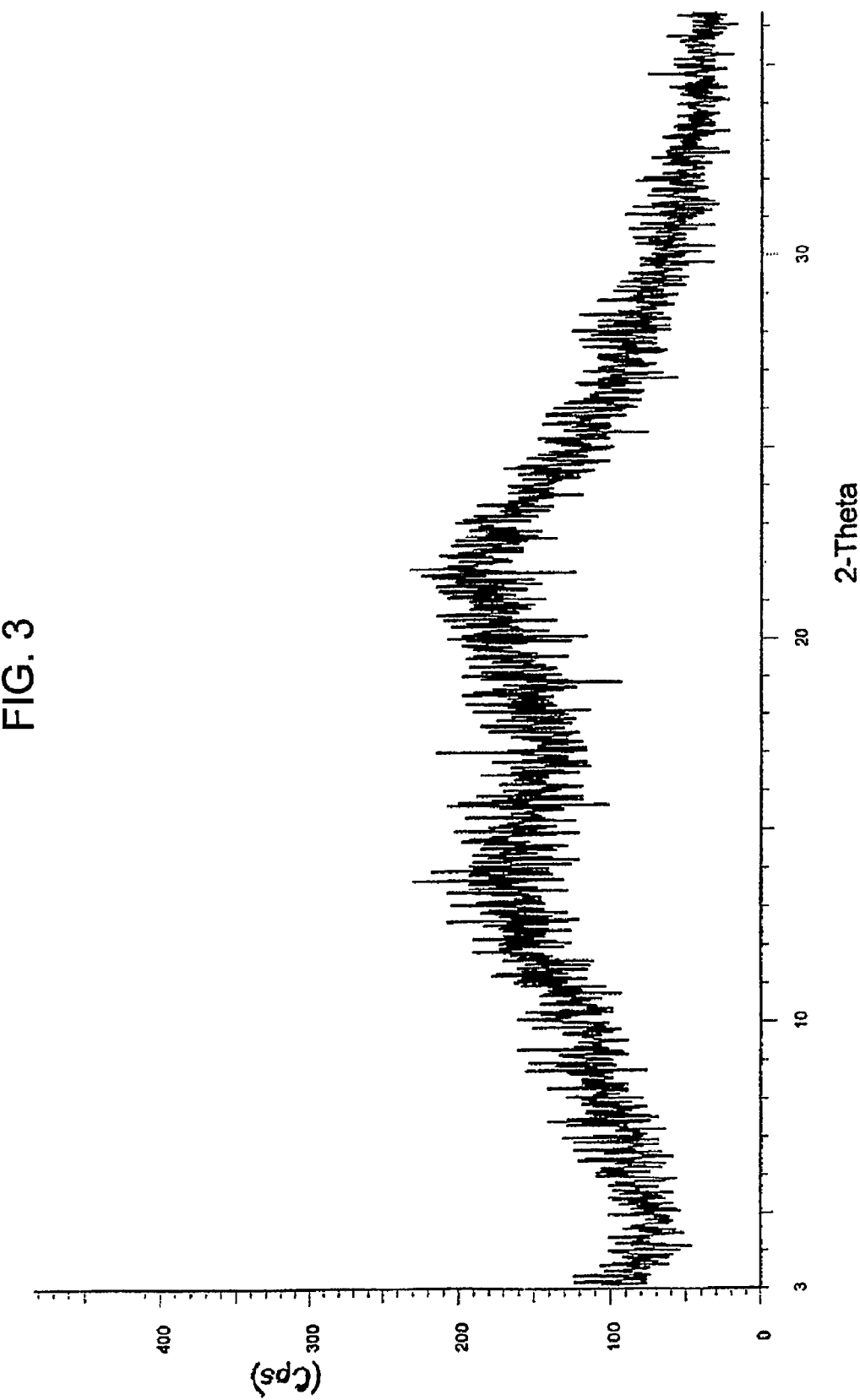
FIG. 3 is an XRPD pattern for amorphous methyl-4'-[[(2 n-propyl-4-methyl-6-(1-methyl benzimidazol-2-yl)-benzimidazol-1-yl]-methyl]-biphenyl-2-carboxylate.

The amorphous form of the compound of formula VI is characterized by the XRPD pattern given in FIG. 3.

A process for preparing the amorphous form of the compound of formula VI comprises:
 a) heating methyl-4'-[[(2-n-propyl-4-methyl-6-(1-methyl benzimidazol-2-yl)-benzimidazol-1-yl]-methyl]-biphenyl-2-carboxylate and an alcoholic solvent such as methanol, ethanol, propanol, isopropanol, or a mixture of any two or more thereof, to reflux;
 b) stirring at reflux, such as for about 30-60 minutes, to form a solution;
 c) distilling off the alcohol from the solution of step b) under reduced pressure; and
 d) isolating the separated solid from step c), which is the amorphous form.

Figure 2:
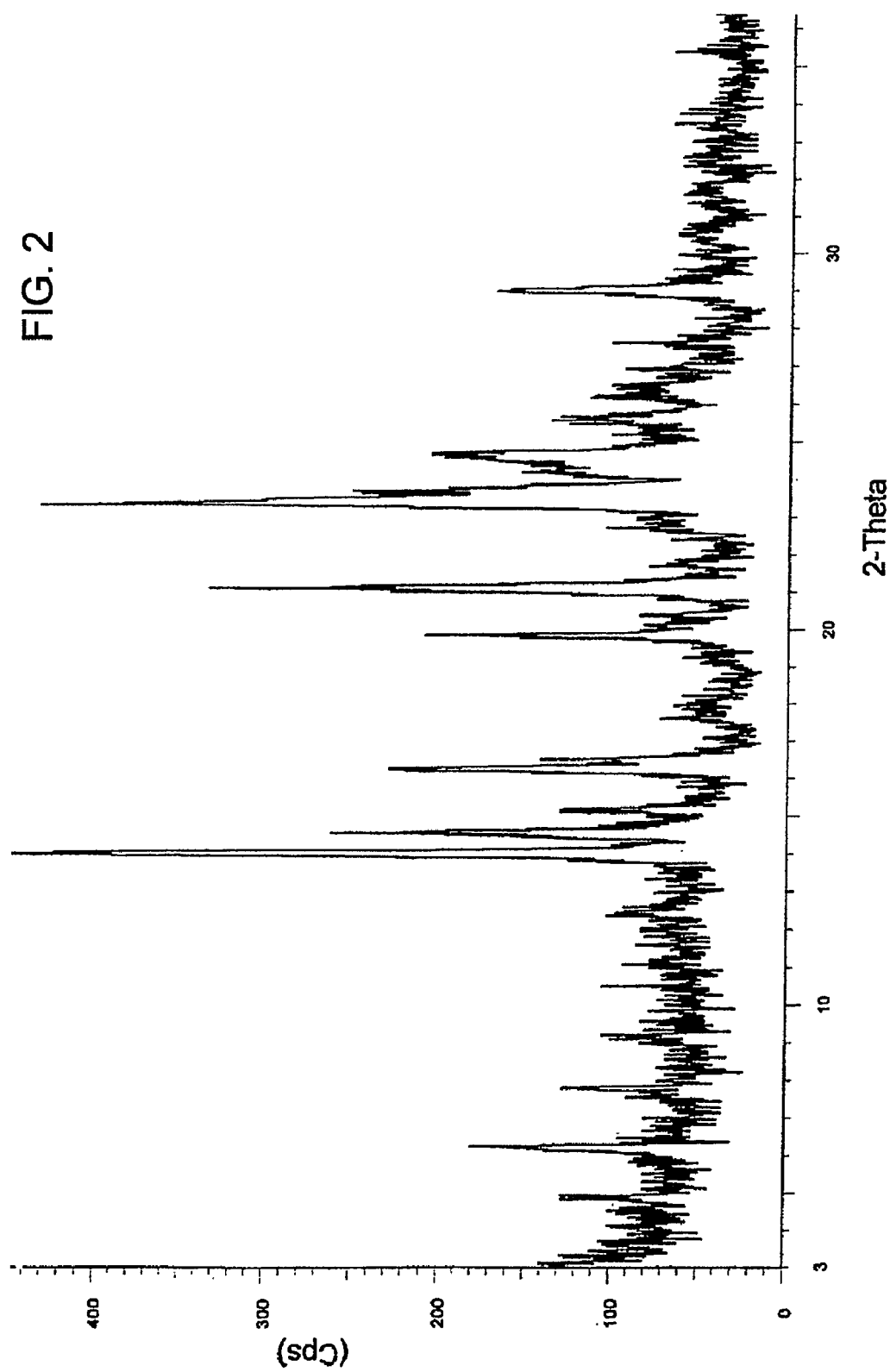
FIG. 2 is an XRPD pattern for the crystalline hydrochloride salt of methyl-4'-[[(2 n-propyl-4-methyl-6-(1-methylbenzimidazol-2-yl)-benzimidazol-1-yl]-methyl]-biphenyl-2-carboxylate.

A crystalline form of the hydrochloride salt of the compound having Formula VI, methyl-4'-[[(2-n-propyl-4-methyl-6-(1-methyl benzimidazol-2-yl)-benzimidazol-1-yl]-methyl]-biphenyl-2-carboxylate hydrochloride is characterized by the XRPD pattern of FIG. 2, wherein the most characteristic peaks are at about 6.1, 12.3, 14.0, 14.5, 16.2, 19.8, 21.1, 23.4, 23.7, 24.2, 24.6, 25.6 and 29.04±0.2 degrees two theta.

A process for preparing the crystalline hydrochloride salt (methyl-4'-[[(2-n-propyl-4-methyl-6-(1-methyl benzimidazol-2-yl)-benzimidazol-1-yl]-methyl]-biphenyl-2-carboxylate hydrochloride) comprises:

a) dissolving methyl-4'-[[(2n-propyl-4-methyl-6-(1-methylbenzimidazol-2-yl)-benzimidazol-1-yl]-methyl]-biphenyl-2-carboxylate in a ketone solvent like acetone, propanone, methyl isobutyl ketone, or a mixture of any two or more thereof, at 25-30° C.;

b) stirring the mixture, such as for about 15-30 minutes, at 25-30° C. to form a solution;

c) adjusting the pH of the solution of step b) to 1-2 by slow addition of hydrochloric acid at 25-30° C.;

d) expelling some part of the solvent from the reaction mass of step c) such as by purging with a gas, such as nitrogen, to cause crystallization;

e) filtering solid formed in step d) and washing with the solvent used in step a); and f) drying the obtained solid from step e) at 45-50° C. to get the crystalline hydrochloride salt of methyl-4'-[[(2-n-propyl-4-methyl-6-(1-methylbenzimidazol-2-yl)-benzimidazol-1-yl]-methyl]-biphenyl-2-carboxylate).

Figure 4:
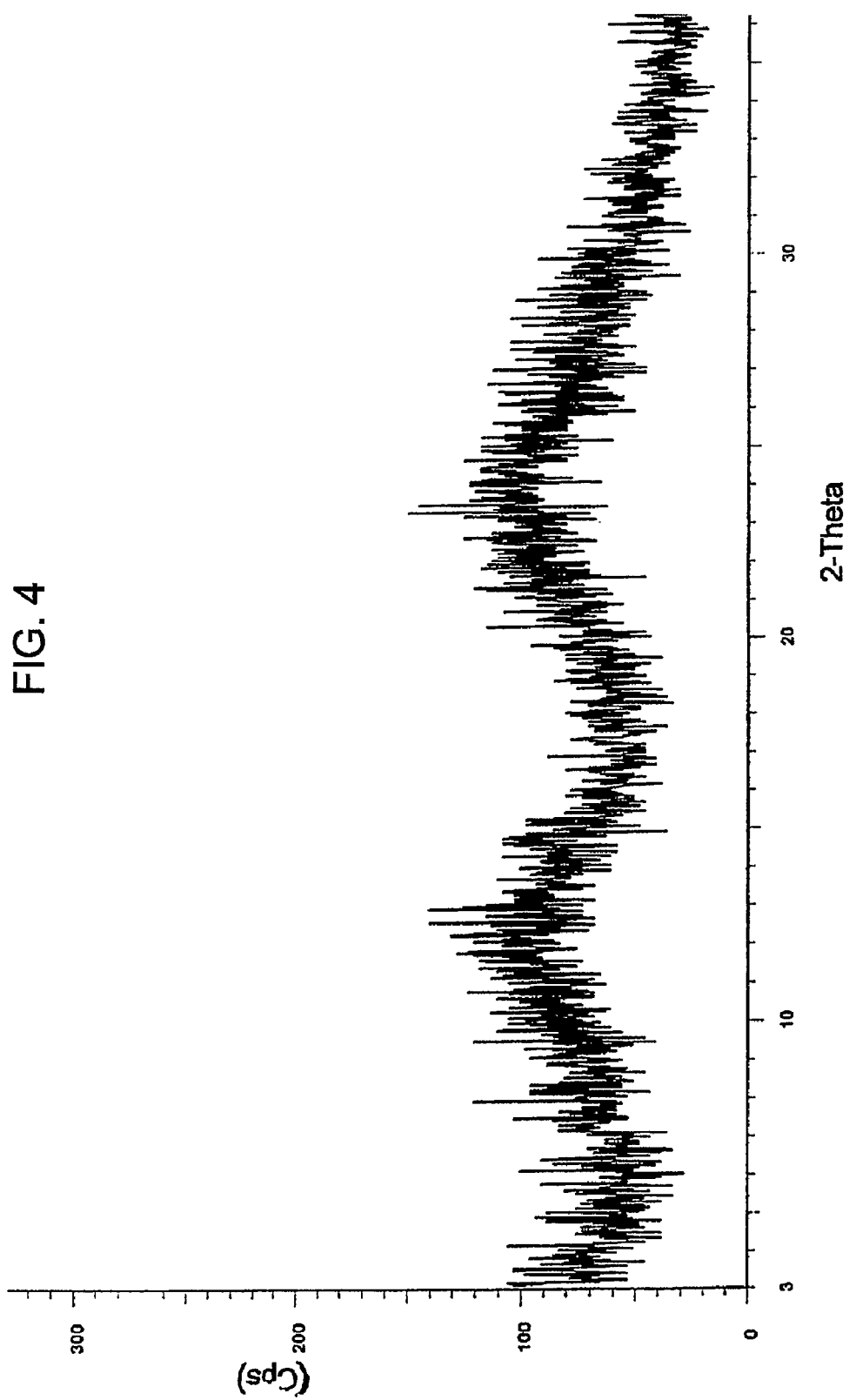
FIG. 4 is an XRPD pattern for the amorphous hydrochloride salt of methyl-4'-[[(2 n-propyl-4-methyl-6-(1-methyl-benzimidazol-2-yl)-benzimidazol-1-yl]-methyl]-biphenyl-2-carboxylate.

The amorphous form of methyl-4'-[[(2-n-propyl-4-methyl-6-(1-methylbenzimidazol-2-yl)-benzimidazol-1-yl]-methyl]-biphenyl-2-carboxylate hydrochloride is characterized by the XRPD pattern given in FIG. 4.

A process for preparing the amorphous form of methyl-4'-[[(2-n-propyl-4-methyl-6-(1-methylbenzimidazol-2-yl)-benzimidazol-1-yl]-methyl]-biphenyl-2-carboxylate hydrochloride comprises:

a) dissolving the hydrochloride salt of methyl-4'-[[(2-n-propyl-4-methyl-6-(1-methylbenzimidazol-2-yl)-benzimidazol-1-yl]-methyl]-biphenyl-2-carboxylate in methanol or acetonitrile;

b) distilling off the solvent from the reaction solution of step a) under reduced pressure;

c) isolation of separated solid from step b);

d) drying the solid from step c) at 25-35° C., such as for about 1-2 hours, to get the amorphous form.

All of the XRPD patterns described herein were obtained using Cu Kα radiation, having the wavelength 1.541 Å. In the figures, values for the x-axis are degrees 2θ.

An additional aspect of the invention provides telmesartan hydrogen sulphate.

In a further aspect, the present invention provides the compounds having Formulas IIb, IIIb, and IVa, and the hydrochloride salt of the compound having Formula VI.

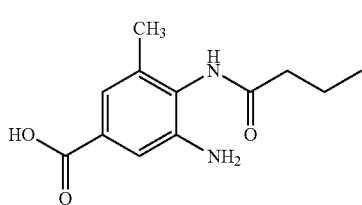

Formula IIb

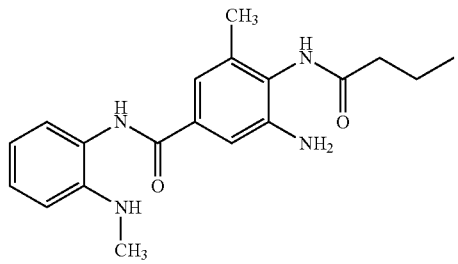

Formula IIIb

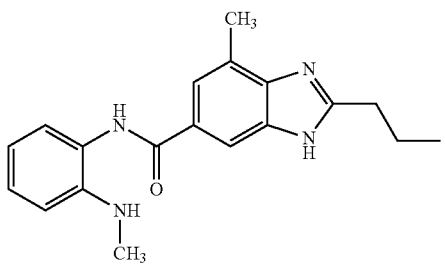

Formula IVa

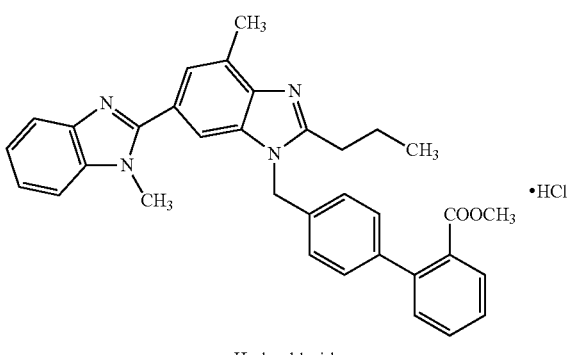

Formula VI

Hydrochloride

In a still further aspect, the invention provides processes for the preparation of compounds having Formulas IIb, IIIb, IVa, and the hydrochloride salt of the compound having Formula VI.

Compound IIb is prepared by process step (a) of the invention described with reference to Scheme B.

Compound IIIb is prepared by process step (a) of the invention described with reference to Scheme C.

Compound IVa is prepared by process step (a) of the invention described with reference to Scheme D.

Compound VI is prepared by process step (d) of the invention described with reference to Scheme A, and the hydrochloride salt is prepared by reacting Compound VI with aqueous hydrochloric acid or an alcoholic hydrochloric acid.

The invention also provides telmisartan containing low concentrations of any one or more of the following impurities:

Methyl-(2-n-propyl-4-methyl-1-hydroxy benzimidazole)-6-carboxylate (Formula VII).

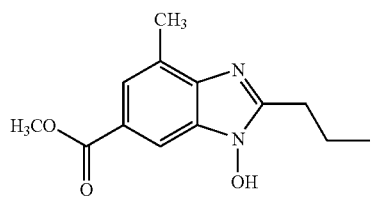

2-n-propyl-4-methyl-1-hydroxy benzimidazole)-6-carboxylic acid (Formula VIII)

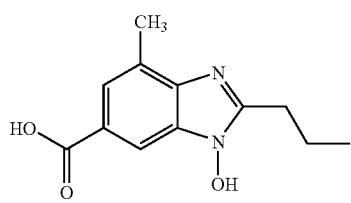

N-methyl-2-nitroso aniline (Formula IX).

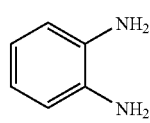

o-Phenylene diamine (Formula X).

N6-[2-(methylamino)phenyl]-3-amino-4-methyl-2-propyl benzo diimidazole-6-carboxamide (Formula IVa).

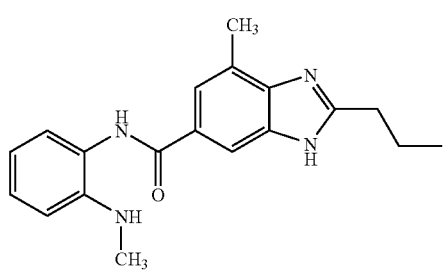

N1-[2-(methylamino)phenyl]-3-amino-4-butyramido-5-methylbenzamide (Formula IIIb).

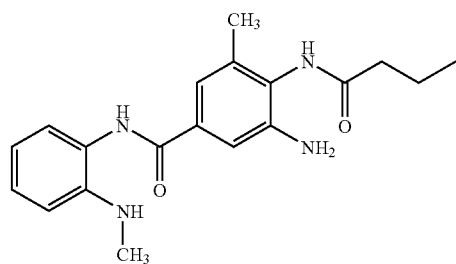

2-n-propyl-4-methyl-6-(1-benzimidazole-2-yl)benzimidazole (Formula XI).

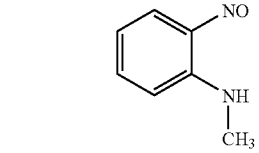

2-n-propyl-4-methyl-6-(1-methyl benzimidazole-2-yl)-1-hydroxy benzimidazole (Formula XII).

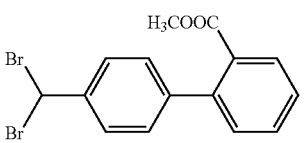

Methyl $4^1,4^1$-dibromo methyl biphenyl-2-carboxylate (Formula XIII).

Methyl 4'-[2-n propyl-4-methyl-6-carboxylic acid-benzimidazol-1-yl]-methyl-biphenyl-2-carboxylate (Formula XIV).

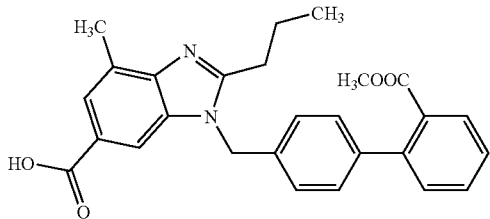

4'-[2-n propyl-4-methyl-6-carboxylic acid-benzimidazol-1-yl]-methyl-biphenyl-2-carboxylic acid (Formula XV).

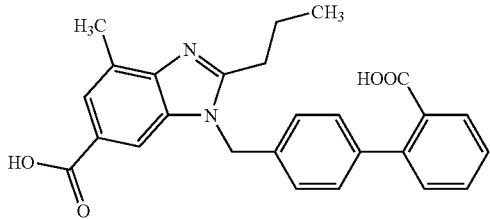

Methyl 4'-[2-n propyl-4-methyl-6{methyl-4"-(1-methyl-biphenyl-2'carboxylate)benzimidazol-2-yl}-benzimidazol-1-yl]-methyl-biphenyl-2-carboxylate (Formula XVI).

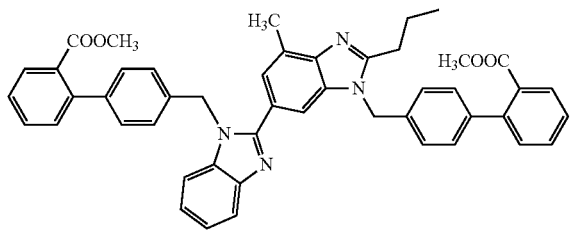

4'-[2-n propyl-4-methyl-6{4"-(1-methyl-biphenyl-2-carboxylic acid)benzimidazol-2-yl}-benzimidazol-1-yl]-methyl-biphenyl-2-carboxylic acid (Formula XVII).

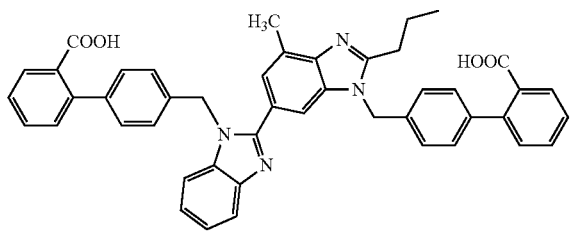

In the context of the invention, a "low concentration" not associated with a specific numeric value is considered to be an amount of an impurity not exceeding about 0.1 area-%, or about 0.05 area-%, of the prepared intermediate, telmisartan, or telmisartan salt, as determined by HPLC.

The following examples are provided to illustrate certain aspects of the invention in greater detail, and are not to be construed as limiting the invention in any manner.

EXAMPLE 1

Preparation of 2-n-propyl-4-methyl-benzimidazole-6-carboxylic Acid

Formula III 11 kg of methyl 4-butyramido-3-methyl-5-nitrobenzoate was dissolved in 165 L of methanol and added to a slurry of water (1 L) and palladium on charcoal (1.02 kg, containing about 50% water by weight). Hydrogen gas was applied to the reaction mass at 3.0-3.5 kg/cm² pressure at 25-35° C. for about 5-6 hours. Reaction completion was confirmed by thin layer chromatography. Filtered the reaction mass through a leaf, online, and micro filter system and washed with 55 L of methanol followed by washing with 50 L of water. Distilled the solvent from the filtrate at a pressure below 600 mm/Hg and a temperature of below 65° C. until 15-20 L of reaction mass volume remained. 110 L of water were added to the residue. 3.58 kg of sodium hydroxide in 22 L of water was added to the reaction mass and heated to 95-100° C. for about 4-5 hours. 44 L of water was added to the reaction mass at 25-30° C. and pH was adjusted to 4.5-5 with a mixture of 36% aqueous hydrochloric acid (8.5 L) and water (8.5 L). Stirred the reaction mass for about 35-45 minutes at 25-30° C. Centrifuged the solid and washed with 44 L of water followed by 33 L of acetonitrile. Dried the solid at 60-70° C. under reduced pressure of about 600-650 mm/Hg for about 4-5 hours to obtain 8.06 kg of the title compound.

EXAMPLE 2

Preparation of 2-n-propyl-4-methyl-6-(1-methyl benzamidazole-2-yl)benzamidazole

Formula IV 7 kg of 2-n-propyl-4-methyl-benzimidazole-6-carboxylic acid, obtained in Example 1, and 6.2 kg of N-methyl-o-phenylenediamine hydrochloride were charged into a reactor containing 21 kg of polyphosphoric acid (PPA) under stirring. Reaction mass was heated to 150-155° C. and maintained at the same temperature for 5-6 hours. Reaction completion was confirmed by thin layer chromatography. Cooled the reaction mass to 90-100° C. 70 L of water was added slowly to the reaction mass at below 100° C. and then cooled to 60-70° C. Stirred at same temperature for 45-60 minutes and then cooled to 40-45° C. 140 L of water was added to the reaction mass and pH was adjusted to 5.5-6 with 50% aqueous sodium hydroxide solution. Centrifuged the reaction mass and washed the solid with 35 L of water.

Charged the wet cake and 70 L of water into a reactor. Reaction mass was heated to 70-80° C. and stirred for 30-45 minutes. Cooled the reaction mass to 40-45° C., centrifuged the solid and washed the cake with 35 L of water. Repeated the above water slurry process one more time, then dried the material at 70-75° C. for 5-6 hours.

Charged the dry material into a reactor containing 80 L of tetrahydrofuran under stirring. Heated the mass to reflux and stirred for 10 minutes. Cooled the reaction mass to 5-10° C. and stirred for 60-90 minutes. Filtered the solid and washed with 9 L of tetrahydrofuran. Dried the material at 70-75° C. under vacuum for 4-5 hours to get 5.9 kg of the title compound.

EXAMPLE 3

Preparation of methyl-4'-[[(2 n-propyl-4-methyl-6-(1-methylbenzimidazol-2-yl)-benzimidazol-1-yl]-methyl]-biphenyl-2-carboxylate hydrochloride Formula VI 7 kg of 2-n-propyl-4-methyl-6-(1-methyl benzimidazole-2-yl)benzimidazole (obtained from Example 2), 11.2 kg of methyl 4'-(bromomethyl)-biphenyl-2-carboxylate, and 1.96 kg of potassium hydroxide were added to 49 L of acetone and stirred at 25-35° C. for 2-3 hours. Centrifuged the reaction mass and washed the solid with 14 L of acetone. Wet solid was dissolved in 35 L of methanol. The pH was adjusted to 1 to 1.5 with methanolic hydrochloric acid solution (12 kg) then stirred for about 20-30 minutes. Filtered the clear solution through a Hyflow (flux calcined diatomaceous earth) bed and washed with 21 L of methanol. Distilled the solvent from filtrate under reduced pressure at below 65° C., until 10-15 L of the reaction mass volume remained. Residue was dissolved in 112 L of acetonitrile and stirred for 1-2 hours at 25-35° C. Centrifuged the solid and washed with 14 L of acetonitrile. Dried the solid at 50-55° C. under vacuum for about 3-4 hours to get 7.94 kg of the title compound.

EXAMPLE 4

Figure 5:
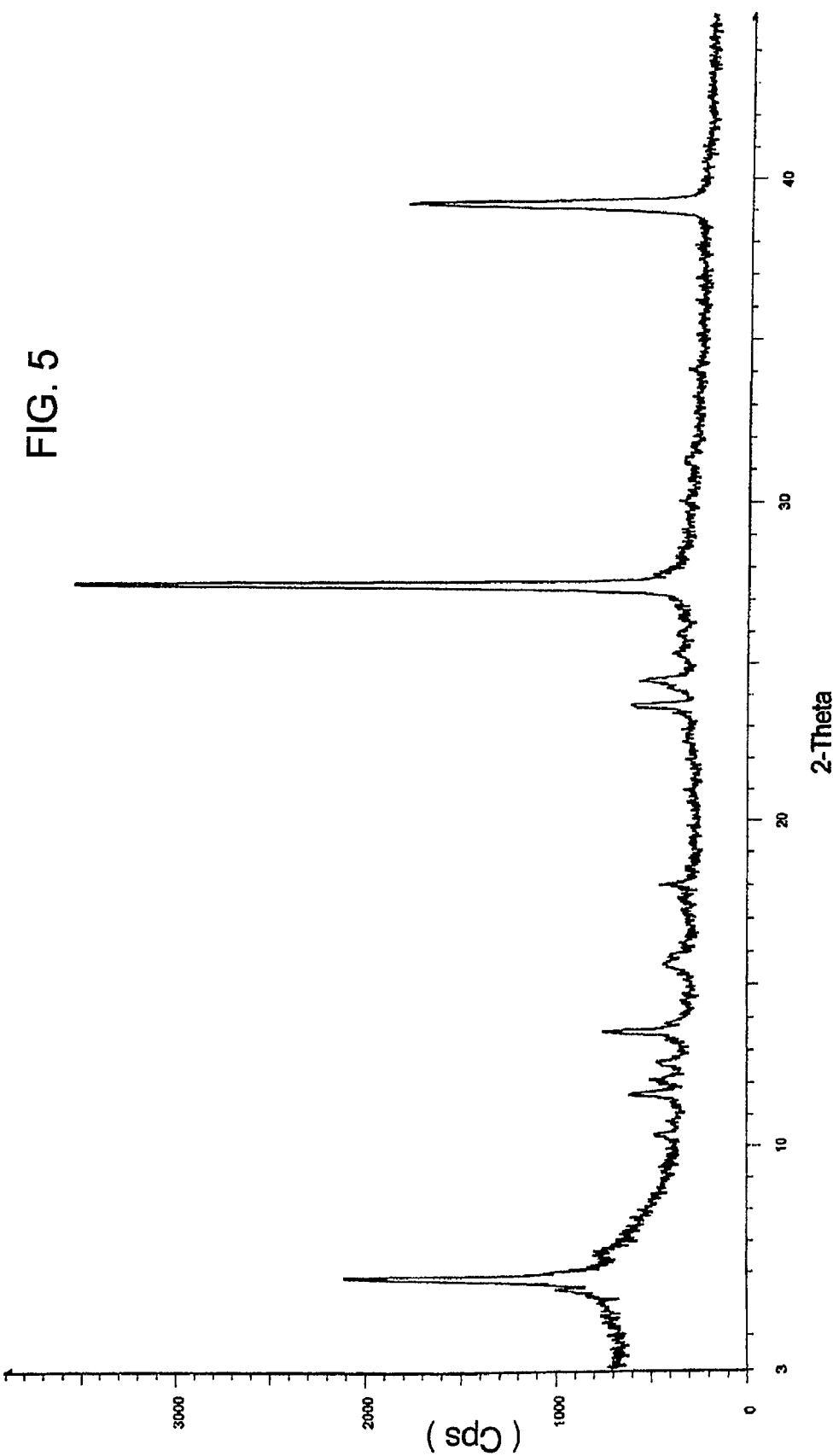
FIG. 5 is an XRPD pattern for the potassium salt of telmisartan.

Preparation of 4'-[(2 n-propyl-4-methyl-6-(1-methyl benzimidazol-2yl)-benzimidazol-1-yl)-methyl]-biphenyl-2-carboxylic acid Telmisartan of Formula I 8 kg of 4'-[[(2-n-propyl-4-methyl-6-(1-methylbenzimidazol-2-yl)-benzimidazol-1-yl]-methyl]-biphenyl-2-carboxylate hydrochloride (obtained from Example 3) was added to the solution of 3.4 kg of potassium hydroxide flakes in 120 L of acetonitrile, in a reactor. Heated the mixture to 70-75° C. and maintained for 2-3 hours. Cooled the reaction mass to 50-55° C. and 0.8 kg of potassium hydroxide flakes were added. Again heated the contents to 70-75° C. and maintained for 1-2 hours. Reaction completion was confirmed by thin layer chromatography. Cooled the mass to 25-35° C. Centrifuged the solid and washed with 16 L of acetonitrile to get telmisartan potassium. After drying, a sample of the telmisartan potassium had the XRPD pattern of FIG. 5.

Charged the wet telmisartan potassium cake and 136 L of water into a reactor and stirred at 25-35° C. for 10-20 minutes. Charged 40 L of acetonitrile and stirred at 25-35° C. for 35-45 minutes. Heated the reaction mass to 40-45° C. and pH was adjusted to 5-5.5 with a mixture of acetic acid (3.5 L) and water (35 L). Maintained the reaction at same temperature for 3-5 hours. Filtered the solid and washed with 16 L of water.

Charged the above wet cake into a reactor containing 120 L of water and heated to 70-75° C. Maintained at same temperature for 35-45 minutes and then cooled to 40-50° C. Filtered the solid and washed with 16 L of water. Dried the material at 70-75° C. for 5-6 hours to get 5.16 kg of crude telmisartan.

Charged the crude telmisartan into a reactor containing a mixture of 56 L of dichloromethane and 24 L of methanol. Stirred at 25-35° C. for 10-20 minutes to get a clear solution. Reaction mass pH was adjusted to 5-5.5 with a mixture of acetic acid (0.2 L) and water (0.2 L). Maintained the reaction mass at 25-35° C. for 35-45 minutes. 0.6 kg of activated charcoal was charged, then the mixture was heated to 36-40° C. and maintained at same temperature for 35-45 minutes. Filtered the reaction mass through online and micro filters at 36-40° C. and washed the reactor with a mixture of dichloromethane (12 L) and methanol (12 L). Distilled the dichloromethane until the temperature reached 45-50° C. at atmospheric pressure, then cooled the reaction mass to 35-40° C. and charged 52 L of methanol. Again distilled dichloromethane under atmospheric pressure until the temperature reached 58-62° C. Finally applied vacuum for 10-15 minutes. Cooled the mass to 25-35° C. and maintained for 35-45 minutes. Filtered the solid and washed with 16 L of methanol. Finally washed the solid with 10 L of water. Dried the material at 75-80° C. for 5-6 hours to afford 4.32 kg of telmisartan.

Figure 7:
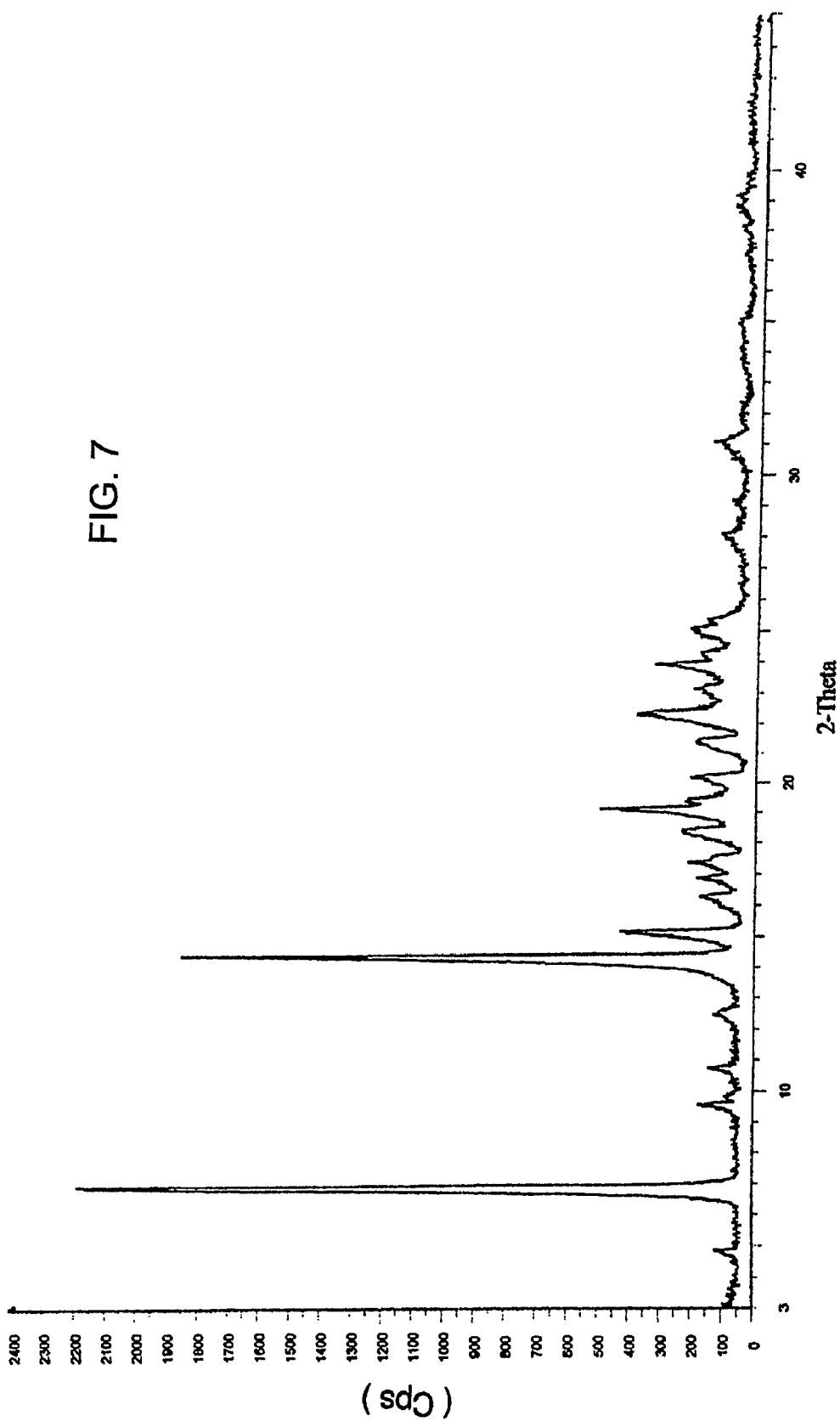
FIG. 7 is an XRPD pattern for telmisartan, prepared according to the invention.

4.5 kg of telmisartan obtained as above was charged into a clean reactor containing 450 L of methanol. Heated the reaction contents to 75-85° C. under closed conditions and maintained at same temperature and the resulting pressure of 2 kg/cm$^2$ for 30-45 minutes. The clear solution thus obtained was passed through online and micro filters and the reactor was washed with 42.5 L of methanol. Cooled the filtrate and washings to 55-65° C. and distilled off the methanol below 65° C. under vacuum until 40-50% of the reaction mass volume remained. Then cooled the reaction mass to 5-10° C. and stirred for 35-45 minutes. Centrifuged the mass and washed the solid with 4.5 L of methanol. Dried the solid at 75-80° C. for 5-6 hours to get 4.0 kg of pure termisartan, having the XRPD pattern of FIG. 7.

EXAMPLE 5

Alternate Process for Preparing 2-n-propyl-4-methyl-benzimidazole-6-carboxylic acid Formula III Step A: Preparation of 3-amino-4-butyramido-5-methyl benzoic acid Formula IIB 10.0 g of methyl 3-amino-4-butyramido-5-methylbenzoate was dissolved in 100 ml of methanol and 3.2 g of sodium hydroxide, and 32 ml of water were added. The contents were heated to 60-65° C. until completion of the reaction. Distilled the solvent from the reaction solution under reduced pressure. The residue was dissolved in 100 ml of water and pH of the resulting solution was adjusted to 1 to 2 with 8 ml of hydrochloric acid at 25-35° C. and stirred for about 2 hours. The separated solid was filtered and washed with 20 ml of water. Dried the solid at 50-55° C. to a constant weight, yielding the title compound.

$^1$H NMR (200 MHz, DMSO): 0.97 (t, 3H), 1.7 (m, 2H), 2.4 (t, 2H), 9.0 (s, NH), 6.9-7.2 (s, 2×Ar—H), 3.3 (s, 3H), 12.5 (s, 1H), 4.9 (s, 2H). Mass: 236 (M$^+$).

Step B: Preparation of 2-n-propyl-4-methyl-benzimidazole-6-carboxylic acid

Formula III 10.0 g of 3-amino-4-butyramido-5-methylbenzoic acid, obtained as in step A, was added to 110 ml of glacial acetic acid and heated to 60-65° C. until completion of the reaction. Distilled the solvent from the reaction solution under reduced pressure. The residue was dissolved in 100 ml of water and added 100 ml of toluene with stirring. Organic layer was separated and washed with (2×100 ml) of water. Distilled the solvent under reduced pressure to get the title compound. (Yield 3.8 g).

EXAMPLE 6

Alternate Process for Preparing 2-n-propyl-4-methyl-6-(1-methyl benzamidazole-2-yl) benzamidazole Formula IV Step A: preparation of 3-amino-4-(butyramido)-5-methyl-N-(2-(methylamino)phenyl)benzamide Formula IIIB 15 g of 3-amino-4-butyramido-5-methylbenzoic acid of Formula IIb, obtained in Example 5, 2.0 g of N-methyl o-phenylenediamine, 150 ml of dichloromethane, 8.6 g of dicyclohexyl carbodiimide (DCC), and 2.9 g of dimethylaminopyridine were combined and stirred for about 15 minutes. Heated the mixture to reflux and maintained until completion of the reaction, and then cooled to room temperature. Filtered the reaction mass and washed with 75 ml of dichloromethane. Diluted the organic layer with 150 ml of water and adjusted the pH to 1-2 with 36% aqueous hydrochloric acid. Extracted the aqueous layer with dichloromethane (75 ml) and then with diethyl ether (3×150 ml). Organic layer was separated and pH was adjusted to 8-10 with 20% aqueous sodium carbonate solution. Again extracted the aqueous layer with 75 ml of dichloromethane. Total organic layer was mixed, washed with water (2×150 ml) and distilled the solvent from the organic layer under reduced pressure. 30 ml of acetone was added to the residue and stirred at 25-30° C. for the separation of the solid. Filtered the solid and washed with acetone (15 ml). Dried the compound at 50-55° C. to get 5.0 g of the title compound.

$^1$H NMR (200 MHz, DMSO): 1.0 (t, 3H), 1.2 (m, 2H), 1.7 (t, 2H), 6.5-7.3 (s, 2×Ar—CH), 6.5-7.3 (d, 2×Ar—H), 6.5-7.3 (t, 2×Ar—H) 9.0 (s, 1H), 2.8 (s, 2H), 2.5 (s, 3H), 9.3 (s, 1H), 5.5 (s, 1H), 2.15 (s, 3H).

Mass: 341.1 (M$^+$).

Step B: Preparation of 2-n-propyl-4-methyl-6-(1-methyl benzamidazole-2-yl) benzamidazole Formula IV 2 g of 3-amino-4-butyramido-5-methyl-N-(2-(methylamino)phenyl)benzamide from step A and 6 g of polyphosphoric acid were charged into a flask and heated to 150-155° C. Stirred at same temperature until completion of the reaction and then cooled to 70-80° C. 20 ml of water was added to the reaction mass and stirred till clear solution was obtained. Reaction mass pH was adjusted to 5-6 with a solution of sodium hydroxide (9 g) in 16 ml of water. Stirred for 30-45 minutes, filtered the solid and washed with 10 ml of water. Dried the solid at 50-55° C. for 4-5 hours to get 0.9 g of the title compound.

EXAMPLE 7

Alternate Process for Preparing 2-n-propyl-4-methyl-6-(1-methyl benzamidazole-2-yl) benzamidazole Formula IV Step A: Preparation of 7-methyl-N-(2-(methylamino)phenyl)-2-propyl-3H-benzodiimidazole-5-carboxamide Formula IVA 15 g of 2-n-propyl-4-methyl-benzimidazole-6-carboxylic acid of Formula III, obtained in Example 1, 2.0 g of N-methyl o-phenylenediamine, 150 ml of dichloromethane, 7.8 g of dicyclohexyl carbodiimide (DCC), and 2.7 g of dimethylaminopyridine were stirred for about 15 minutes. Heated the reaction mass to reflux and maintained until completion of the reaction, and then cooled to room temperature. Filtered the reaction mass and washed with 75 ml of dichloromethane. Distilled the solvent from the filtrate under vacuum and added 30 ml of acetone to the residue. Stirred at 25-35° C. for the separation of the solid, filtered the solid and washed with acetone (15 ml). Dried the solid at 50-55° C. to get 6.0 g of the title compound.

$^1$H NMR (200 MHz, DMSO): 0.99 (t, 3H), 1.8 (m, 2H), 2.8 (t, 2H), 6.5-8.2 (s, 2×Ar—CH), 6.5-8.2 (d, 2×Ar—H), 6.5-8.2 (t, 2×Ar—H) 12.4 (s, 1H), 2.5 (s, 3H), 9.5 (s, 1H), 3.3 (s, 3H).

Mass: 323.4 (M$^+$).

Step B: Preparation of 2-n-propyl-4-methyl-6-(1-methyl benzamidazole-2-yl) benzamidazole Formula IV 2 g of 7-methyl-N-(2-(methylamino)phenyl)-2-propyl-3H-benzodiimidazole-5-carboxamide (Formula IVa) from step A and 6 g of polyphosphoric acid were charged into a flask and heated to 150-155° C. Stirred at same temperature till the completion of reaction and then cooled to 70-80° C. 20 ml of water was added to the reaction mass and stirred till clear solution was obtained. Reaction mass pH was adjusted to 5-6 with a solution of sodium hydroxide (9 g) in 16 ml of water. Stirred for 30-45 minutes, filtered the solid and washed with 10 ml of water. Dried the solid at 50-55° C. for 4-5 hours to get 1.2 g of the title compound.

EXAMPLE 8

Preparation of Crystalline Form A of methyl-4'-[[(2-n-propyl-4-methyl-6-(1-methylbenzimidazol-2-yl)-benzimidazol-1-yl]-methyl]-biphenyl-2-carboxylate Formula VI 4 grams of methyl-4'-[[(2-n-propyl-4-methyl-6-(1-methyl-benzimidazol-2-yl)-benzimidazol-1-yl]-methyl]-biphenyl-2-carboxylate and 40 ml of acetonitrile was refluxed for 30 minutes. Half of the solvent was evaporated under reduced pressure. The remaining mass was cooled to 25-30° C. with stirring for 30-45 minutes. Filtered the separated solid and washed with acetonitrile (8 ml). Dried the solid at 50-55° C. for 3-4 hours to get the title crystalline form, having the XRPD pattern of FIG. 1. (Yield: 4 grams).

EXAMPLE 9

Preparation of the Crystalline Hydrochloride Salt of methyl-4'-[[(2-n-propyl-4-methyl-6-(1-methylbenzimidazol-2-yl]-benzimidazol-1-yl]-methyl]-biphenyl-2-carboxylate 10 g of the hydrochloride salt of methyl-4'-[[(2n-propyl-4-methyl-6-(1-methylbenzimidazol-2-yl)-benzimidazol-1-yl]-methyl]-biphenyl-2-carboxylate, prepared as described in Example 3, was dissolved in 300 ml of acetone with stirring. The pH of the reaction solution was adjusted to 1-2 by slow addition of 15 ml of hydrochloric acid at 25-30° C. 200 ml of the acetone was evaporated from the reaction mass by passing nitrogen gas through the solution. Filtered the separated solid and washed with acetone (20 ml). Dried the obtained solid at 50-55° C. to get the title crystalline compound, having the XRPD pattern of FIG. 2. (Yield: 9.8 grams).

EXAMPLE 10

Preparation of the Amorphous Form of methyl-4'-[[(2-n-propyl-4-methyl-6-(1-methylbenzimidazol-2-yl)-benzimidazol-1-yl]-methyl]-biphenyl-2-carboxylate Formula VI 3 g of methyl-4'-[[(2-n-propyl-4-methyl-6-(1-methylbenzimidazol-2-yl)-benzimidazol-1-yl]-methyl]-biphenyl-2-carboxylate and 45 ml of methanol was refluxed for 30 minutes. The solvent was evaporated under reduced pressure. Scraped the solid from the container to get the title amorphous form, having the XRPD pattern of FIG. 3.

EXAMPLE 11

Preparation of the Amorphous Form of the Hydrochloride Salt of methyl-4'-[[(2-n-propyl-4-methyl-6-(1-methylbenzimidazol-2-yl)-benzimidazol-1-yl]-methyl]-biphenyl-2-carboxylate 3 g of the hydrochloride salt of methyl-4'-[[(2n-propyl-4-methyl-6-(1-methylbenzimidazol-2-yl)-benzimidazol-1-yl]-methyl]-biphenyl-2-carboxylate was dissolved in 15 ml of methanol with stirring. The solvent was evaporated under reduced pressure. Scraped the solid from the container and dried at 25-30° C. to get the title amorphous form, having the XRPD pattern of FIG. 4.

EXAMPLE 12

Preparation of methyl 4'-(bromomethyl)biphenyl-2-carboxylate

Formula V 10 kg of methyl-4-methylbiphenyl-2-carboxylate, 9 kg of 1,3-dibromo-5,5-dimethyl hydantoin (DBDMH), and 0.5 kg azo-bis-isobutyronitrile (AIBN) were charged into a reactor containing 100 L of chloroform under stirring. The mixture was slowly heated to 55-61° C. and maintained for 30-45 minutes. Reaction completion was confirmed by thin layer chromatography. Cooled the mass to 25-35° C. Filtered the reaction mass through a Hyflow bed and washed with chloroform (10 L). Filtrate was washed with water (2×100 L) and distilled the solvent below 60° C. under vacuum. Residue was cooled to 30-40° C. and charged a mixture of 45 L of n-hexane and 5 L of isopropanol. Reaction mass was cooled to −5 to 0° C. and stirred for 2-3 hours. Filtered the solid and washed with 10 L of chilled n-hexane. Dried the solid at 25-35° C. under vacuum to afford 11.5 kg of the title compound.

EXAMPLE 13

Preparation of methyl-(2-n-propyl-4-methyl-1-hydroxy benzimidazole)-6-carboxylate Formula VII 50 g of 4-butyramido-3-methyl-5-nitrobenzoate was charged into a clean dry round bottom flask containing 500 ml of methanol. Charged 101.4 g of $SnCl_2$ followed by slow addition of 100 ml of 36% aqueous hydrochloric acid. Reaction mass was heated to reflux and maintained for 2-3 hours. Distilled the solvent completely under vacuum at below 70° C. and then charged 500 ml of water. Cooled the reaction mass to room temperature and pH was adjusted to 8-10 with 20% aqueous sodium hydroxide solution. Stirred for 30-45 minutes at room temperature, filtered the solid and washed with 100 ml of water. Charged the wet solid and 500 ml of water into the flask. Heated to 70-80° C. and stirred for 30-45 minutes. Cooled to 25-35° C. and stirred for 30-45 minutes. Filtered the solid and washed with 100 ml water. Dried the solid at 50-55° C. for 4-5 hours to afford 28 g of the title compound.

$^1$H NMR (200 MHz, DMSO): 0.97 (t, 3H), 1.84 (m, 2H), 2.87 (t, 2H), 12.2 (s, OH), 7.5-7.8 (s, 2×Ar—H), 3.78 (s, 3H), 3.78 (s, 3H), 3.9 (s, 3H).

Mass: 249.3 ($M^+$).

EXAMPLE 14

Preparation of (2-n-propyl-4-methyl-1-hydroxy benzimidazole)-6-carboxylic acid

Formula VIII 25 g of methyl-(2-n-propyl-4-methyl-1-hydroxy benzimidazole)-6-carboxylate of Example 12 was charged into a round bottom flask containing 250 ml methanol. Charged 7.5 g of sodium hydroxide flakes and heated the reaction mass to reflux. Stirred at reflux for 1-2 hours and then distilled the solvent completely. 250 ml of water was charged and the mass cooled to 25-35° C. Reaction mass pH was adjusted to 1-2 with 10 ml of 36% of aqueous hydrochloric acid and stirred for 30-45 minutes. Filtered the solid and washed with water (50 ml). Dried the solid at 50-55° C. for 4-5 hours to afford 12 g of the title compound.

$^1$H NMR (200 MHz, DMSO): 1.02 (t, 3H), 1.9 (m, 2H), 3.06 (t, 2H), 7.7-7.9 (s, 2×Ar—H), 3.69 (s, 1H), 2.5 (s, 2H).

Mass: 235.5 ($M^+$).

EXAMPLE 15

Preparation of 2-n-propyl-4-methyl-6-(1-benzimidazol-2-yl)benzimidazole

Formula XI 5 g of 2-n-propyl-4-methyl-benzimidazole-6-carboxylic acid of Formula III, obtained in Example 1, and 2.6 g of o-phenylenediamine, were charged into a round bottom flask containing 15 g of polyphosphoric acid (PPA). Reaction mass was heated to 150-155° C. and maintained for 4-5 hours. Cooled the reaction mass to 70-80° C. and charged 50 ml of water. Stirred for 45-60 minutes at the same temperature and then cooled to 10-15° C. Reaction mass pH was adjusted to 5-6 with 10% aqueous sodium hydroxide solution (200 ml) and stirred for 15-30 minutes. Filtered the solid and washed with 10 ml of water.

The wet solid was charged into a flask and 50 ml of water was added. The contents were heated to 70-80° C. and stirred for 30-45 minutes. Cooled to 25-35° C. and stirred for 30-45 minutes. Filtered the solid and washed with 10 ml of water. Dried the solid at 50-55° C. for 4-5 hours to afford 7.2 g of the title compound.

$^1$H NMR (200 MHz, DMSO): 0.95 (t, 3H), 1.8 (m, 2H), 2.8 (t, 2H), 7.0-8.2 (s, 2×Ar—CH), 7.0-8.2 (d, 2×Ar—H), 7.0-8.2 (t, 2×Ar—H) 12.4 (s, 1H), 2.45 (s, 3H), 12.8 (s, 1H).

Mass: 291.0 (M$^+$).

EXAMPLE 16

Preparation of 2n-propyl-4-methyl-6-(1-methyl benzimidazole-2-yl)-1-hydroxy benzimidazole Formula XII 5 g of (2-n-propyl-4-methyl-1-hydroxy benzimidazole)-6-carboxylic acid of Formula VIII and 3.5 g N-methyl-o-phenylene diamine hydrochloride, was charged into a round bottom flask containing 15 g of polyphosphoric acid (PPA). Reaction mass was heated to 150-155° C. and maintained for 4-5 hours. Cooled the reaction mass to 70-80° C. and charged 50 ml of water. Stirred for 45-60 minutes at the same temperature and then cooled to 10-15° C. Reaction mass pH was adjusted to 5-6 with 50% aqueous sodium hydroxide solution and stirred for 15-30 minutes. Filtered the solid and washed with 25 ml of water.

The wet solid was charged into a flask and 50 ml of water was added. The contents were heated to 70-80° C. and stirred for 30-45 minutes. Cooled to 25-35° C. and stirred for 30-45 minutes. Filtered the solid and washed with 25 ml of water. Dried the solid at 50-55° C. for 4-5 hours to afford 3.4 g of the title compound.

$^1$H NMR (200 MHz, DMSO): 1.0 (t, 3H), 1.8 (m, 2H), 2.9 (t, 2H), 7.0-8.0 (s, 2×Ar—CH), 7.0-8.0 (d, 2×Ar—H), 7.0-8.0 (t, 2×Ar—H) 11.5 (s, 1H), 3.5 (s, 3H), 3.9 (s, 3H). Mass: 321.0 (M$^+$).

EXAMPLE 17

Preparation of methyl 4'-[2-n-propyl-4-methyl-6-carboxylic acid-benzimidazol-1-yl]-methyl-biphenyl-2-carboxylate Formula XIV 10 g of 2-n-propyl-4-methyl-benzimidazole-6-carboxylic acid of Example 1, 19.8 g of 4'-(bromomethyl)biphenyl-2-carboxylate, and 6.4 g of potassium hydroxide were charged into a round bottom flask containing 100 ml of N,N-dimethyl acetamide. The contents were heated to 80-85° C. and stirred for 2-3 hours. Reaction completion was confirmed by thin layer chromatography and the mass was cooled to 25-35° C. Charged 100 ml of water and extracted the product with ethyl acetate (3×450 ml). Organic layer was washed with water (2×100 ml) and then the solvent was distilled completely under vacuum. 100 ml of acetone was charged to the residue at room temperature and stirred for 30-45 minutes. Filtered the solid and washed with acetone (20 ml). Dried the solid at 50-55° C. for 4-5 hours to get 21 g of the title compound.

$^1$H NMR (200 MHz, DMSO): 0.99 (t, 3H), 1.2 (m, 2H), 2.9 (t, 2H), 7.0-8.0 (s, 2×Ar—CH), 7.0-8.0 (d, 6×Ar—H), 7.0-8.0 (t, 2×Ar—H), 2.5 (s, 3H), 12.7 (s, 1H), 5.6 (s, 2H), 12.7 (s, 1H).

Mass: 428.9 (M$^+$).

EXAMPLE 18

Preparation of 4'-[2-n-propyl-4-methyl-6-carboxylic acid-benzimidazol-1-yl]-methyl-biphenyl-2-carboxylic acid Formula XV 15 g of the acid ester of Example 14 and 8.4 g of potassium hydroxide were charged into a round bottom flask containing 225 ml of acetonitrile. The contents were heated to 70-75° C. and stirred for 2-3 hours. Reaction completion was confirmed by thin layer chromatography and the solvent was distilled completely under vacuum. Reaction mass was cooled to 25-35° C. and charged 225 ml of water. Reaction mass pH was adjusted to 4-5 with 36% aqueous hydrochloric acid (12 ml) and stirred for 30-45 minutes. Filtered the solid and washed with 30 ml of water.

The wet solid was charged into a flask containing 70 ml of acetonitrile at room temperature. Stirred for 30-45 minutes, filtered the solid and washed with acetonitrile (20 ml). Dried the solid at 25-35° C. for 4-5 hours to get 10 g of the title compound.

$^1$H NMR (200 MHz, DMSO): 0.95 (t, 3H), 1.9 (m, 2H), 3.1 (t, 2H), 7.0-8.2 (s, 2×Ar—CH), 7.0-8.2 (d, 6×Ar—H), 7.0-8.2 (t, 2×Ar—H), 3.6 (s, 3H), 13.2 (s, 1H), 5.4 (s, 2H), 2.3 (s, 3H).

Mass: 443.2 (M$^+$).

EXAMPLE 19

Preparation of methyl 4'-[2-n-propyl-4-methyl-6 {methyl-4"-(1-methyl-biphenyl-2 carboxylate)benzimidazol-2-YL}-benzimidazol-1-yl]-methyl-biphenyl-2-carboxylate Formula XVI 10 g of the compound from Example 15, 17 g of 4'-(bromomethyl)biphenyl-2-carboxylate, and 3 g of potassium hydroxide were charged into a round bottom flask containing 70 ml of acetone. The contents were stirred for 2-3 hours at room temperature. Filtered the solid and washed with 20 ml of acetone. Distilled the solvent from the filtrate completely under vacuum to get a residue.

This residue was eluted with chloroform in a silica gel column and distilled the chloroform completely to get 4 g of the title compound.

$^1$H NMR (200 MHz, DMSO): 1.0 (t, 3H), 1.8 (m, 2H), 2.9 (t, 2H), 6.9-8.0 (s, 2×Ar—CH), 6.9-8.0 (d, 14×Ar—H), 6.9-8.0 (t, 6×Ar—H), 2.7 (s, 3H), 5.3 (s, 2H), 3.5 (s, 3H), 5.4 (s, 2H), 3.6 (s, 3H)

Mass: 739.3 (M$^+$). .

EXAMPLE 20

Preparation of 4'-[2-n-propyl-4-methyl-6{4"-(1-methyl-biphenyl-2-carboxylic acid)benzimidazol-2-yl}-benzimidazol-1-yl]-methyl-biphenyl-2-carboxylic acid Formula XVII 3 g of the acid ester of Example 18 and 0.7 g of sodium hydroxide were charged into a round bottom flask containing 45 ml of water. The contents were heated to 70-75° C. and stirred for 4-5 hours. Reaction completion was confirmed by thin layer chromatography and the mass was cooled to 25-35° C. Reaction mass pH was adjusted to 4-5 with 36% aqueous hydrochloric acid (3 ml) and stirred for 30-45 minutes. Filtered the solid and washed with 15 ml of water. Dried the solid at 50-55° C. for 4-5 hours to get 2.0 g of the title compound.

$^1$H NMR (200 MHz, DMSO): 0.9 (t, 3H), 1.8 (m, 2H), 2.9 (t, 2H), 6.9-7.8 (s, 2×Ar—CH), 6.9-7.8 (d, 14×Ar—H), 6.9-7.8 (t, 6×Ar—H), 3.3 (s, 3H), 5.4 (s, 2H), 12.8 (s, 1H), 5.6 (s, 2H), 12.8 (s, 1H).

Mass: 711.4 (M$^+$).

EXAMPLE 21

Figure 6:
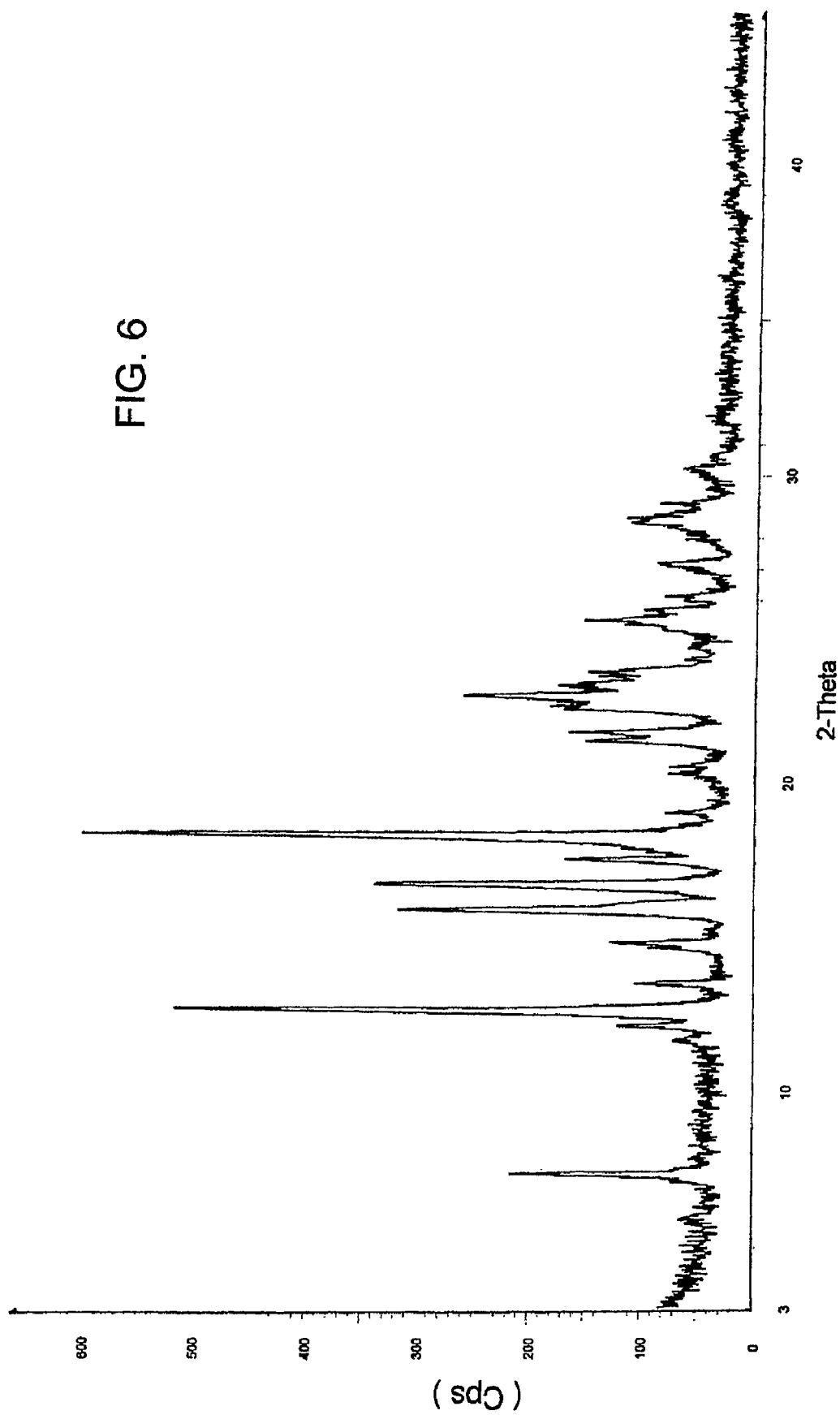
FIG. 6 is an XRPD pattern for the hydrogen sulphate salt of telmisartan.

Preparation of Telmisartan Hydrogen Sulphate 15 g of telmisartan potassium salt, isolated from Example 4, was charged into a round bottom flask containing 225 ml of methanol and stirred for 10-15 minutes. Filtered to remove undissolved solids and washed with 30 ml of methanol. 75 ml of water was added to the filtrate and stirred for 5-10 minutes at 25-35° C. Reaction mass pH was adjusted to 2-2.5 by adding a mixture of sulfuric acid (3 ml) and water (60 ml) and stirring for 10-15 minutes. Charged 150 ml of water to the mass and stirred for 30-45 minutes. Filtered the solid and washed with 75 ml of water. Dried the solid at 70-75° C. for 4-5 hours to get 10.0 g of the title compound as a crystalline solid, having the XRPD pattern of FIG. 6.

The invention claimed is:

1. A process comprising cyclizing 3-amino-4-butyramido-5-methylbenzoic acid to form 2-n-propyl-4-methyl-benzimidazole-6-carboxylic acid.

2. The process of claim 1, further comprising reacting 2-n-propyl-4-methyl-benzimidazole-6-carboxylic acid with N-methyl-o-phenylenediamine or a salt thereof, to form 2-n-propyl-4-methyl-6-(1-methylbenzimidazol-2-yl)benzimidazole.

3. The process of claim 1, further comprising reacting 2-n-propyl-4-methyl-6-(1-methylbenzimidazol-2-yl)benzimidazole with methyl 4'-(bromomethyl)biphenyl-2-carboxylate, to form methyl-4'-[[(2-n-propyl-4-methyl-6-(1-methylbenzimidazol-2-yl)-benzimidazol-1-yl]-methyl]-biphenyl-2-carboxylate.

4. The process of claim 1, further comprising hydrolyzing methyl-4'-[[(2-n-propyl-4-methyl-6-(1-methylbenzimidazol-2-yl)-benzimidazol-1-yl]-methyl]-biphenyl-2-carboxylate to form telmisartan.

5. The process of claim 1, further comprising:
   a) reacting 2-n-propyl-4-methyl-benzimidazole-6-carboxylic acid with N-methyl-o-phenylenediamine, to form 2-n-propyl-4-methyl-6-(1-methylbenzimidazol-2-yl)benzimidazole;
   b) reacting 2-n-propyl-4-methyl-6-(1-methylbenzimidazole-2-yl)benzimidazole with methyl 4'-(bromomethyl)biphenyl-2-carboxylate, to form methyl-4'-[[(2-n-propyl-4-methyl-6-(1-methylbenzimidazol-2-yl)-benzimidazol-1-yl]-methyl-biphenyl-2-carboxylate; and
   c) hydrolyzing methyl-4'-[[(2-n-propyl-4-methyl-6-(1-methyl benzimidazol-2-yl)-benzimidazol-1-yl]-methyl]-biphenyl-2-carboxylate with an acid to form telmisartan.

6. The process of claim 1, wherein 3-amino-4-butyramido-5-methylbenzoic acid is prepared by hydrolyzing methyl 3-amino-4-butyramido-5-methylbenzoate with a base.

7. The process of claim 6, wherein methyl 3-amino-4-butyramido-5-methylbenzoate is prepared by hydrogenating methyl-4-butyramido-3-methyl-5-nitrobenzoate.

8. The process of claim 7, wherein at least one of methyl 3-amino-4-butyramido-5-methylbenzoate and 3-amino-4-butyramido-5-methylbenzoic acid is not isolated.

* * * * *